(12) United States Patent
Wang et al.

(10) Patent No.: US 8,101,290 B2
(45) Date of Patent: Jan. 24, 2012

(54) ORGANIC COMPOUND HAVING ELECTRON-TRANSPORTING AND/OR HOLE-BLOCKING PERFORMANCE AND ITS USE AND OLEDS COMPRISING THE COMPOUND

(75) Inventors: PengFei Wang, Beijing (CN); Na Li, Beijing (CN); Weimin Liu, Beijing (CN); Shuit-Tong Lee, Hong Kong (CN); Chun-Sing Lee, Hong Kong (CN)

(73) Assignee: Technical Institute of Physics and Chemistry of Chinese Academy of Sciences, Beijing (CN)

( * ) Notice: Subject to any disclaimer, the term of this patent is extended or adjusted under 35 U.S.C. 154(b) by 305 days.

(21) Appl. No.: 12/252,153

(22) Filed: Oct. 15, 2008

(65) Prior Publication Data

US 2009/0102356 A1    Apr. 23, 2009

(30) Foreign Application Priority Data

Oct. 17, 2007 (CN) .......................... 2007 1 0176008
Oct. 17, 2007 (CN) .......................... 2007 1 0176009

(51) Int. Cl.
*H01L 51/50* (2006.01)
*C07D 401/10* (2006.01)
*C07D 405/14* (2006.01)
*H01J 1/63* (2006.01)

(52) U.S. Cl. ........ 428/690; 428/917; 313/504; 313/506; 546/255; 546/256

(58) Field of Classification Search ........................ None
See application file for complete search history.

(56) References Cited

U.S. PATENT DOCUMENTS

| | | | |
|---|---|---|---|
| 3,172,862 | A | 3/1965 | Gurnee et al. |
| 3,173,050 | A | 3/1965 | Gurnee |
| 3,710,167 | A | 1/1973 | Dresner et al. |
| 5,247,190 | A | 9/1993 | Friend et al. |
| 5,408,109 | A | 4/1995 | Heeger et al. |
| 5,552,678 | A | 9/1996 | Tang et al. |

FOREIGN PATENT DOCUMENTS

| | | | |
|---|---|---|---|
| CA | 443861 | A | 8/1947 |
| JP | 2005276801 | A | 10/2005 |

OTHER PUBLICATIONS

Ghozlan et al., Tetrahedron, vol. 58, (2002), pp. 9423-9429.*
Dresner, J. "Double Injection Electroluminescence in Anthracene" RCA Review, Jun. 1969, 322-334.
Djurovich et al. "IR(III) Cyclometalated Complexes as Efficient Phosphorescent Emitters in Polymer Blend and Organic LEDs" Polymer Preprints 2000, 41(1), 770-771.

(Continued)

*Primary Examiner* — Dawn L Garrett
(74) *Attorney, Agent, or Firm* — Volpe and Koenig, P.C.

(57) ABSTRACT

Disclosed herein are several organic compounds having electron-transporting and/or hole-blocking performance and their preparation method and use and the OLEDs comprising the organic compound. The organic compounds exhibit high ionization potential (IP), electron affinity (Ea), glass transition temperature (Tg) and high electron mobility, and are a kind of good electron-transporting material with good hole-blocking ability. The devices comprising these compounds as one of the emitting layer, electron-transporting layer (ETL) and hole-blocking layer (HBL) show improved efficiency and better color purity.

8 Claims, 1 Drawing Sheet

OTHER PUBLICATIONS

Baldo et al. "Very High-Efficiency Green Organic Light-Emitting Devices Based on Electrophosphorescence" Applied Physics Letters, vol. 75, No. 1, Jul. 5, 1999, 4-6.

Krohnke, Fritz "The Specific Synthesis of Pyridines and Oligopyridines" Synthesis, Jan. 1976, 1-24.

Kurfurst, Antonin et al. "Oligophenylene 2,4,6-Triarylpyridines and Analogous Diaza-p-Terphenyls, Diaza-p-Quaterphenyls and Diaza-p-Quinquephenyls with Luminiscent Activity" Collect. Czech. Chem. Commun. (vol. 54) 1989 (pp. 462-472).

* cited by examiner

ORGANIC COMPOUND HAVING ELECTRON-TRANSPORTING AND/OR HOLE-BLOCKING PERFORMANCE AND ITS USE AND OLEDS COMPRISING THE COMPOUND

FIELD OF THE INVENTION

This invention relates to a novel organic compound having electron-transporting and/or hole-blocking performance and its use as hole-blocking material and OLEDs comprising the compound.

BACKGROUND OF THE INVENTION

Since the discovery of multi-layered organic light-emitting diodes and organic light-emitting devices (hereafter refer to as OLEDs) by Tang and Van Slyke, OLEDs have become the subjects of intensive investigations because of their applications in full-color displays. In simplest form, an organic light-emitting device is comprised of an anode for hole injection, a cathode for electron injection, and an organic medium sandwiched between these electrodes to support charge recombination that yields emission of light.

These devices are also commonly referred to as OLEDs. Representative of earlier OLEDs are disclosed in Gurnee et al. U.S. Pat. No. 3,172,862 issued on Mar. 9, 1965; Gurnee U.S. Pat. No. 3,173,050 issued on Mar. 9, 1965; Dresner, "Double Injection Electroluminescence in Anthracene", RCA Review, Vol. 30. pp. 322-334, 1969; and Dresner U.S. Pat. No. 3,710,167 issued on Jan. 9, 1973. The organic layers in these OLEDs, usually composed of a polycyclic aromatic hydrocarbon, were very thick (much greater than 1 μm). Consequently, operating voltages were very high, often >100V.

Since then, tremendous efforts have been made to enhance the performance of OLEDs from many aspects. The present inventors have made much progress in the region of OLEDs without doubt. A great deal of new materials, especially RGB (red, green, blue)-light-emitting materials, have been designed and synthesized, and then applied in OLEDs. It is well known to use organic electroluminescent compounds as the light-emitting layer in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, Friend et al, U.S. Pat. No. 5,247,190; Heeger et al., U.S. Pat. No. 5,408,109; and Nakano et al., Published European Patent application 443861. Complexes of 8-hydroxyquinolate with trivalent metal ions, particularly aluminum, have been extensively used as electroluminescent components, as has been disclosed in, for example, Fang et al., U.S. Pat. No. 5,552,678.

Borrows and Thompson have reported that fac-tris(2-phenylpyridine) iridium(Ir(ppy)3) can be used as the electroluminescent component in organic light-emitting devices (Appl. Phys. Lett. 1999, 75, 4.). The performance is maximized when the iridium compound is present in a host conductive material. Thompson has further reported devices in which the light-emitting layer is poly(N-vinyl carbazole) doped with fac-tris [2-(4',5'-difluorophenyl) pyridine-$C'^2$,N] iridium(III). (see Polymer Preprints 2000, 41(1), 770.)

High-efficiency OLEDs depends heavily on charge injection, transport and recombination. Therefore, hole-blocking materials (HBM) and electron-transporting materials (ETM) are also important in devices. Compared with so many HBMs developed, only few good ETMs were reported so far. Now tris(8-hydroxyquinoline)aluminum (Alq3) is a common ETMs for its good stability in devices, however, due to its smaller electron mobility, large number of holes will come into ETM, and then combination with electron in Alq3 layer. As a result, a small mount of light emission from Alq3 is often observed. Thus, it unavoidably leads to bad color purity. 1,3,5-tris(phenyl-2-benzimidazolyl)benzene (TPBI) is another efficient ETM. However, it is a crystalline compound. It is well-known that crystallization is a serious problem in OLEDs. 2,9-dimethyl-4,7-diphenylphenathroline (BCP) which has high ionization potential (IP) is a very good hole-blocking material (HBM). Nevertheless its bad electron-transporting ability, BCP can not be used as ETM solely.

Therefore, it is very much demanding for good electron-transporting material with high hole-blocking performance to improve efficiency and color purity.

SUMMARY OF THE INVENTION

One object of the present invention is to provide a novel organic compound having electron-transporting and/or hole-blocking performance and its use as hole-blocking material of the same. The other object is to provide OLEDs which address some of the problems discussed above. In particular, the OLEDs which use the novel organic compound provided by the present invention as electron-transporting layer (ETL) and/or hole-blocking layer (HBL) provide good color purity and improved efficiency.

The present invention provides a novel organic compound having electron-transporting and/or hole-blocking performance, wherein said compound is one of multi-aryl substituted pyridine derivatives represented by the following formulas (a)-(f):

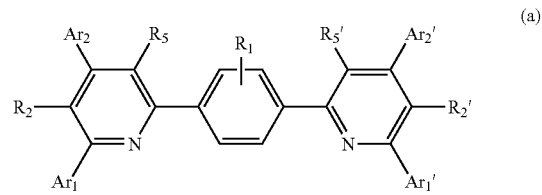

(a)

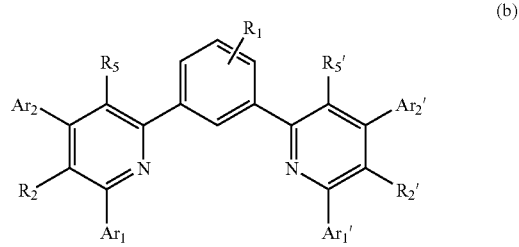

(b)

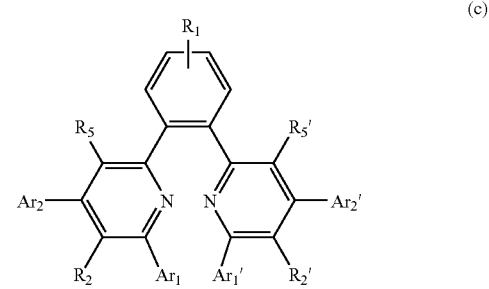

(c)

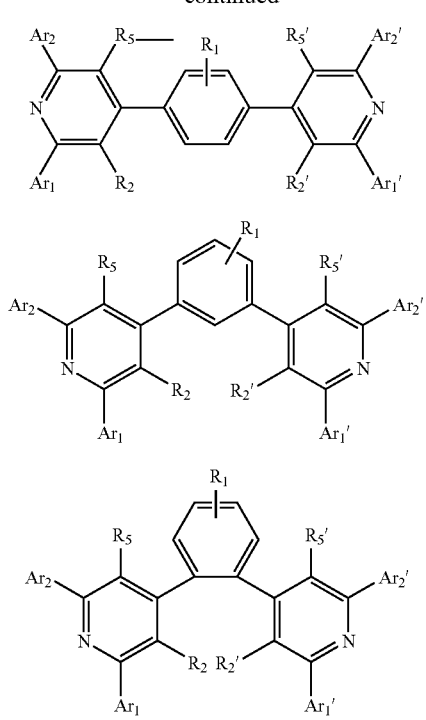

wherein,

R$_1$ in each formula is independently selected from the group consisting of hydrogen, substituted or unsubstituted C$_1$-C$_{20}$ alkyl, substituted or unsubstituted C$_3$-C$_{20}$ cyclic alkyl, substituted or unsubstituted C$_1$-C$_{20}$ alkoxy, C$_7$-C$_{50}$ aralkyl, C$_6$-C$_{50}$ aryl, C$_6$-C$_{50}$ aryloxy and heterocyclic aryl;

R$_2$, R$_2$', R$_5$, R$_5$' in each formula are independently selected from the group consisting of hydrogen, carboxyl, fluorinated methyl, cyano, nitro and C$_2$-C$_{20}$ ester group, and at least contain one of carboxyl, fluorinated and cyano group, and R$_2$, R$_2$', R$_5$, R$_5$' in each formula may be same or different;

Ar$_1$, Ar$_1$', Ar$_2$ Ar$_2$' in each formula are independently selected from the group consisting of C$_6$-C$_{50}$ aryl or C$_5$-C$_{50}$ heterocyclic aryl, and Ar$_1$, Ar$_1$', Ar$_2$, Ar$_2$' in each formula may be same or different.

The present invention further provides the use of the organic compound having electron-transporting and/or hole-blocking performance provided by the present invention as hole-blocking material, emitting material and electron material.

The present invention also provides the use of the organic compound having electron-transporting and/or hole-blocking performance of any one of claims 1-3 in organic semiconductor devices such as organic transistor, organic integrated circuit, organic solar cell, organic laser or organic sensor.

The present invention also provides an OLED comprising an anode, a cathode, a luminescent layer, at least one hole-transporting layer disposed between said anode and said luminescent layer, at least one electron-transporting layer disposed between said cathode and said luminescent layer, and a substrate present on either the anode or cathode, wherein at least one of said electron-transporting layer comprises the organic material having electron-transporting and/or hole-blocking performance provided by the present invention.

The present invention also provides an OLED comprising an anode, a cathode, an electron-emitting layer disposed between said anode and said cathode, at least one hole-transporting layer disposed between said anode and said electron-emitting layer, at least one electron-transporting layer disposed between said cathode and said electron-emitting layer, a hole-blocking layer between the electron-emitting layer and the electron-transporting layer, and a substrate present on either the anode or cathode, wherein at least one of said electron-transporting layer comprises the organic compound having electron-transporting and/or hole-blocking performance provided by the present invention.

The OLEDs provided by the present invention possesses an unexpectedly improved efficiency and narrow emission band. For example, the OLED using diethyl 6,6'-(1,4-phenylene)bis(2,4-diphenylnicotinonitrile)(PBDNN) as ETL with the structure of ITO/NPB(75 nm)/ADN:TBP(30 nm)/PBDNN (35 nm)/LiF(0.5 nm)/MgAg(100 nm) gives a deep blue emission of the CIE x=0.15 y=0.22 which is closer to standard deep blue than which uses tris(8-hydroxyquinoline)aluminum (AlQ3) as ETL. This surprising feature of the present invention provides an improved blue emitting organic light-emitting device with exceptionally high color purity and efficiency. Certainly the organic compound having electron-transporting and/or hole-blocking performance can be used in other devices, for example, doping fluorescent device, phosphorescent device, white OLEDs and so on. Furthermore, the compound and materials provided by the present invention are easy to be prepared, and thus are economically attractive.

Figure 1:
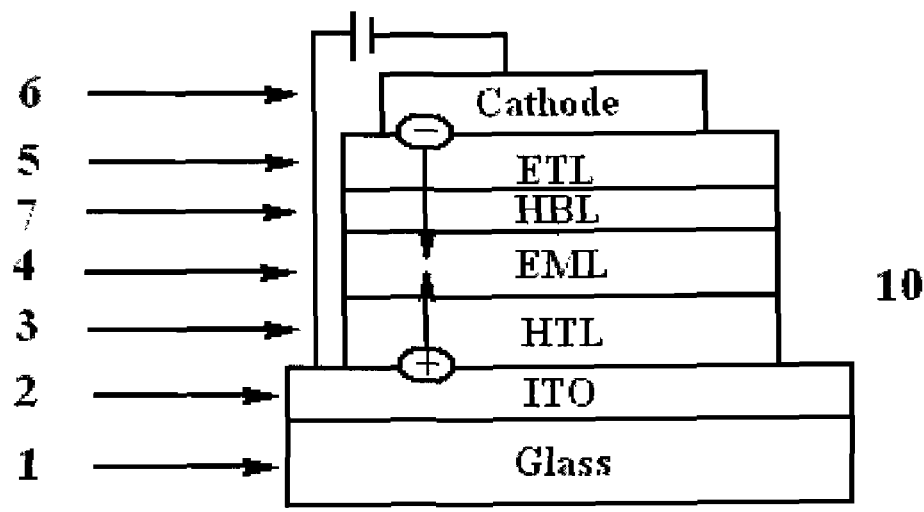
FIG. 1 illustrates a diagram of the structure of the conventional OLEDs.

Reference numeral 1 indicates a substrate; numeral 2 indicates an anode; numeral 3 indicates an organic hole-transporting layer (HTL); numeral 4 indicates an organic emitting layer (EML); numeral 5 indicates an organic electron-transporting layer (ETL); numeral 6 indicates a cathode, numeral 7 indicates an organic hole-blocking layer (HBL) and numeral 10 indicates the OLEDs.

DETAILED DESCRIPTION OF THE PREFERRED EMBODIMENTS

The present invention relates to an organic compound having electron-transporting and/or hole-blocking performance, the preparation method and use thereof and the OLEDs comprising the organic compound having electron-transporting and/or hole-blocking performance provided by the present invention.

According to the present invention, the new organic compound having electron-transporting and/or hole-blocking performance is one of multi-aryl substituted pyridine derivatives represented by formulas (a)-(f) as mentioned above. Preferably, the new organic compound having electron-transporting and/or hole-blocking performance is one or more multi-aryl substituted pyridine derivatives represented by formulas (g)-(1):

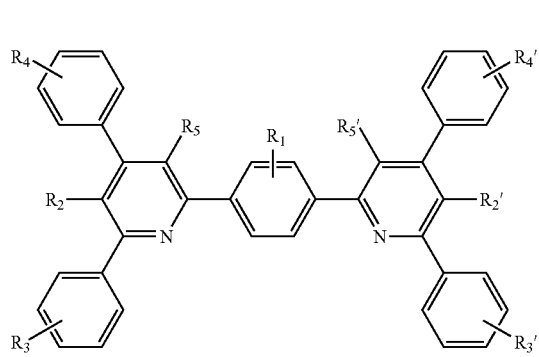
(g)

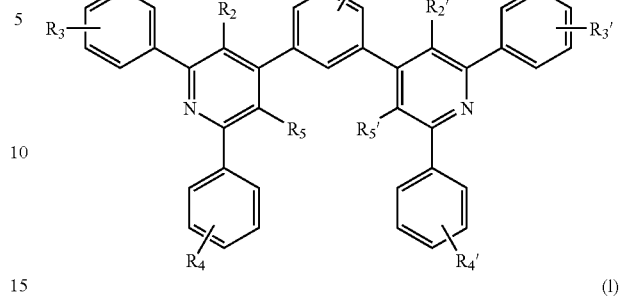
(k)

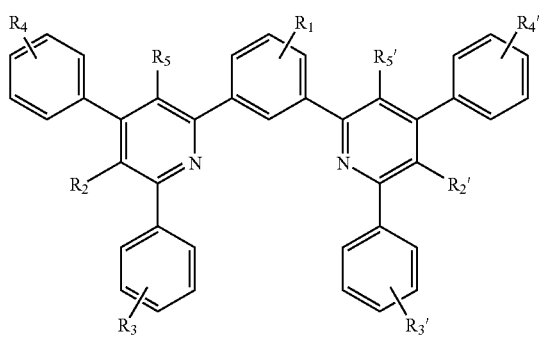
(h)

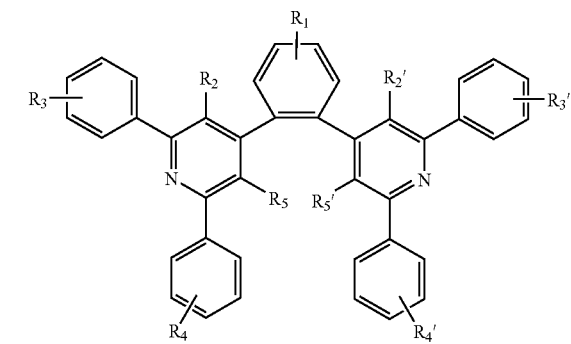
(l)

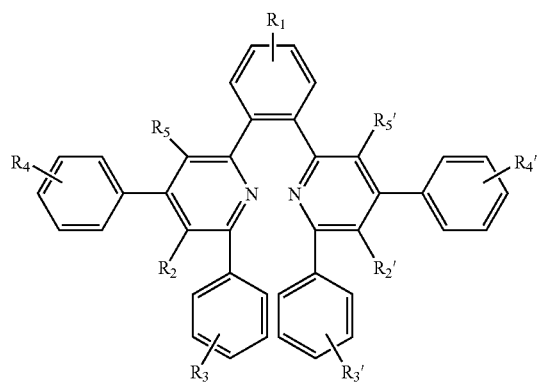
(i)

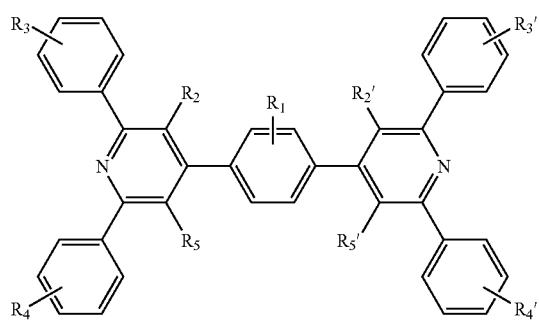
(j)

wherein:

$R_1$, $R_3$, $R_3'$, $R_4$, $R_4'$ in each formula is independently selected from the group consisting of hydrogen, substituted or unsubstituted $C_1$-$C_{20}$ alkyl, substituted or unsubstituted $C_3$-$C_{20}$ cyclic alkyl, substituted or unsubstituted $C_1$-$C_{20}$ alkoxy, $C_7$-$C_{50}$ aralkyl, $C_6$-$C_{50}$ aryl, $C_6$-$C_{50}$ aryloxy and $C_5$-$C_{50}$ heterocyclic aryl;

$R_2$, $R_2'$, $R_5$, $R_5'$ in each formula are independently selected from the group consisting of hydrogen, carboxyl, fluorinated methyl, cyano, nitro and $C_2$-$C_{20}$ ester group, and at least contain one of carboxyl, fluorinated and cyano group;

$Ar_1$, $Ar_1'$, $Ar_2$, $Ar_2'$ in each formula are independently selected from the group consisting of $C_6$-$C_{50}$ aryl and heterocyclic aryl.

Preferably, $R_1$, $R_3$, $R_3'$, $R_4$, $R_4'$ in each formula is independently selected from the group consisting of hydrogen, substituted or unsubstituted $C_1$-$C_{10}$ alkyl, substituted or unsubstituted $C_3$-$C_{10}$ cyclic alkyl, substituted or unsubstituted $C_1$-$C_{10}$ alkoxy, $C_7$-$C_{30}$ aralkyl, $C_6$-$C_{30}$ aryl, $C_6$-$C_{30}$ aryloxy and $C_5$-$C_{50}$ heterocyclic aryl;

$R_2$, $R_2'$, $R_5$, $R_5'$ in each formula are independently selected from the group consisting of hydrogen, carboxyl, fluorinated methyl, cyano, nitro and $C_2$-$C_{10}$ ester group, and at least contain one of carboxyl, fluorinated methyl and cyano group;

$Ar_1$, $Ar_1'$, $Ar_2$, $Ar_2'$ in each formula are independently selected from the group consisting of $C_6$-$C_{30}$ aryl and $C_5$-$C_{30}$ heterocyclic aryl.

The terms unsubstituted $C_1$-$C_{20}$ alkyl may be methyl, ethyl, propyl, isopropyl, n-butyl, sec-butyl, isobutyl, tert-butyl, n-pentyl, n-hexyl, n-heptyl or n-octyl.

The terms substituted $C_1$-$C_{20}$ alkyl may be hydroxymethyl, 1-hydroxyethyl, 2-hydroxyethyl, 2-hydroxy-isobutyl, 1,2-dihydroxy-ethyl, 1,3-dihydroxy-isopropyl, 2,3-dihydroxy-tert-butyl, 1,2,3-trihydroxy-propyl, chloromethyl, 1-chloroethyl, 2-chloroethyl, 1-chloropropyl, 2-chloropropyl, 3-chloropropyl, 2-chloroisobutyl, 1,2-dichloroethyl, 1,3-dichloro-isopropyl, 2,3-dichloro-tert-butyl, 1,2,3-trichloropropyl, bromomethyl, 1-bromoethyl, 2-bromoethyl, 1-bromopropyl, 2-bromopropyl, 3-bromopropyl, 2-bromo-isobutyl, 1,2-dibromoethyl, 2-bromo-isobutyl, 1,2-dibromoethyl, 1,3-dibromo-isopropyl, 2,3-dibromo-tert-butyl, 1,2,3-tribromopropyl, iodomethyl, 1-iodoethyl, 2-iodoethyl, 2-iodoisobutyl, 1,2-diiodoethyl, 1,3-diiodo-isopropyl, 2,3-diiodo-tert-butyl, 1,2,3-triiodopropyl, aminomethyl, 1-aminoethyl, 2-amino-tert-ethyl, 2-amino-isobutyl, 1,2-diaminoethyl, 1,3-diaminoisopropyl, 2,3-diamino-tert-butyl or 1,2,3-triaminopropyl.

The terms unsubstituted $C_3$-$C_{20}$ cyclic alkyl may be cyclopropyl, cyclobutyl, cyclopentyl or cyclohexyl.

The terms substituted $C_3$-$C_{20}$ cyclic alkyl may be 4-methyl-cyclohexyl, adamantyl or norbornyl.

The terms $C_1$-$C_{20}$ alkoxy from which $R_1$, $R_3$, $R_3'$, $R_4$, $R_4'$ are selected may be represented by —OR, wherein R represents alkyl group which includes methyl, ethyl, propyl, isopropyl, n-butyl, sec-butyl, isobutyl, tert-butyl, n-pentyl, n-hexyl, n-heptyl, n-octyl, hydroxymethyl, 1-hydroxyethyl, 2-hydroxyethyl, 2-hydroxy-isobutyl, 1,2-dihydroxy-ethyl, 1,3-dihydroxy-isopropyl, 2,3-dihydroxy-tert-butyl, 1,2,3-trihydroxy-propyl, chloromethyl, 1-chloroethyl, 2-chloroethyl, 2-chloroisobutyl, 1,2-dichloroethyl, 1,3-dichloro-isopropyl, 2,3-dichloro-tert-butyl, 1,2,3-trichloropropyl, bromomethyl, 1-bromoethyl, 2-bromoethyl, 2-bromo-isobutyl, 1,2-dibromoethyl, 2-bromo-isobutyl, 1,2-dibromoethyl, 1,3-dibromo-isopropyl, 2,3-dibromo-tert-butyl, 1,2,3-tribromopropyl, iodomethyl, 1-iodoethyl, 2-iodoethyl, 2-iodo-isobutyl, 1,2-diiodoethyl, 1,3-diiodo-isopropyl, 2,3-diiodo-tert-butyl, 1,2,3-triiodopropyl, aminomethyl, 1-aminoethyl, 2-aminoethyl, 2-amino-isotutyl, 1,2-diaminoethyl, 1,3-diaminoisopropyl, 2,3-diamino-tert-butyl, 1,2,3-triaminopropyl, cyanomethyl, 1-cyanoethyl, 2-cyanoethyl, 2-cyano-isobutyl, 1,2-dicyanoethyl, 1,3-dicyano-isopropyl, 2,3-dicyano-tert-butyl, 1,2,3-tricyanopropyl, nitromethyl, 1-nitroethyl, 2-nitroethyl, 2-nitro-isobutyl, 1,2-dinitroethyl, 1,3-dinitro-isopropyl, 2,3-dinitro-tert-butyl or 1,2,3-trinitropropyl.

The terms $C_7$-$C_{50}$ aralkyl may be benzyl, 1-phenylethyl, 2-phenylethyl, 1-phenyl-isopropyl, 2-phenyl-isopropyl, phenyl-tert-butyl, α-naphthyl-methyl, 1-α-naphthylethyl, 2-α-naphthylethyl, 1-α-naphthyl-isopropyl, 2-α-naphthyl-isopropyl, β-naphthylmethyl, 1-β-naphthylethyl, 2-β-naphthylethyl, 1-β-naphthyl-isopropyl, 2-β-naphthyl-isopropyl, 1-pyrrylmethyl, 2-(1-pyrryl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-chloro-2-phenyl-isopropyl or triphenylmethyl.

The terms $C_6$-$C_{50}$ aryl may be phenyl, 1-naphthyl, 2-naphthyl, 1-anthracenyl, 2-anthracenyl, 9-anthracenyl, 1-phenanthryl, 2-phenanthryl, 3-phenanthryl, 4-phenanthryl, 9-phenanthryl, 1-tetraphenyl, 2-tetraphenyl, 9-tetraphenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthracene, 4'-methyl-biphenyl or 4"-tert-butyl-p-terphenyl-4-yl.

The terms $C_6$-$C_{50}$ aryloxyl may be represented by —OAr, wherein Ar represents the aryl group which includes phenyl, 1-naphthyl, 2-naphthyl, 1-anthracenyl, 2-anthracenyl, 9-anthracenyl, 1-phenanthryl, 2-phenanthryl, 3-phenanthryl, 4-phenanthryl, 9-phenanthryl, 1-tetraphenyl, 2-tetraphenyl, 9-tetraphenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthracene, 4'-methyl-biphenyl, 4"-tert-butyl-p-terphenyl-4-yl, 2-pyrrolyl, 3-pyrrolyl, 1-pyridyl, 2-pyridyl, 3-pyridyl, 4-pyridyl, 2-indolyl, 3-indolyl, 4-indolyl, 5-indolyl, 6-indolyl, 7-indolyl, 8-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 5-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenathiazinyl, 2-phenathiazinyl, 3-phenathiazinyl, 4-phenathiazinyl, 1-phenoxazinyl, 2-phenoxazinyl, 3-phenoxazinyl, 4-phenoxazinyl, 2-oxazol, 4-oxazol, 5-oxazol, 2-oxadiazol, 5-oxadiazol, 3-furazano, 2-trienyl, 3-trienyl, 2-methylpyridine-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-tert-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl.

The terms $C_5$-$C_{50}$ heterocyclic aryl may be 2-pyrrolyl, 3-pyrrolyl, 1-pyridyl, 2-pyridyl, 3-pyridyl, 4-pyridyl, 2-indolyl, 3-indolyl, 4-indolyl, 5-indolyl, 6-indolyl, 7-indolyl, 8-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 5-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenathiazinyl, 2-phenathiazinyl, 3-phenathiazinyl, 4-phenathiazinyl, 1-phenoxazinyl, 2-phenoxazinyl, 3-phenoxazinyl, 4-phenoxazinyl, 2-oxazol, 4-oxazol, 5-oxazol, 2-oxadiazol, 5-oxadiazol, 3-furazano, 2-trienyl, 3-trienyl, 2-methylpyridine-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-tert-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl.

The terms fluorinated methyl may be fluoromethy, difluoromethy or trifluoromethy.

The terms $C_2$-$C_{20}$ ester group may be methyl ester group, ethyl ester group, propyl ester group, isopropyl ester group, n-butyl ester group, sec-butyl ester group, isobutyl ester group, n-hexyl ester group, n-heptyl ester group or n-octyl ester group.

The terms $C_6$-$C_{50}$ aryl may be phenyl, 1-naphthyl, 2-naphthyl, 1-anthracenyl, 2-anthracenyl, 9-anthracenyl, 1-phenanthryl, 2-phenanthryl, 3-phenanthryl, 4-phenanthryl, 9-phenanthryl, 1-tetraphenyl, 2-tetraphenyl, 9-tetraphenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthracene, 4'-methyl-biphenyl or 4"-tert-butyl-p-terphenyl-4-yl.

The terms $C_5$-$C_{50}$ heterocyclic aryl may be 2-pyrrolyl, 3-pyrrolyl, 1-pyridyl, 2-pyridyl, 3-pyridyl, 4-pyridyl, 2-indolyl, 3-indolyl, 4-indolyl, 5-indolyl, 6-indolyl, 7-indolyl, 8-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 5-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenathiazinyl, 2-phenathiazinyl, 3-phenathiazinyl, 4-phenathiazinyl, 1-phenoxazinyl, 2-phenoxazinyl, 3-phenoxazinyl, 4-phenoxazinyl, 2-oxazol, 4-oxazol, 5-oxazol, 2-oxadiazol, 5-oxadiazol, 3-furazano, 2-trienyl, 3-trienyl, 2-methylpyridine-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-tert-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl.

In formulas (a)-(l), $R_1$, $R_3'$ and $R_4'$ can be linked with the aromatic ring at any unoccupied aromatic ring forming atoms including the o-, m- and p-positions.

The organic compound having electron-transporting and/or hole-blocking performance provided by the present invention represented by one of formulas (a)-(c) can be prepared by the method comprises the following steps:

(1) at the temperature of −10° C. to 40° C., adding one or more of the bromo ketone represented by formulas (A1)-(B1) and pyridine into a first solvent, stirring for 10-15 hours, then bromopyridinium is obtained, wherein the molar ratio of the bromo ketone to pyridine is 1:0.8-2;

(2) in the atmosphere of inert gases, adding the bromopyridinium obtained in step (1), the aromatic diketone represented by formula (C1), one or more of aromatic aldehyde represented by formulas (D1) and (E1), and catalysis amount ammonium salt, into a second solvent, then refluxing for 20-30 hours, the resulted crude product is purified by silicon gel chromatography column or recrystallization, wherein the molar ratio of the bromopyridinium, the aromatic diketone and the aromatic aldehyde is (2-3): 1:(2-3).

The organic compound having electron-transporting and/or hole-blocking performance provided by the present invention represented by one of formulas (d)-(f) can be prepared by the method comprises the following steps:

(I) at the temperature of −10° C. to 40° C., adding one or more of the bromo ketone represented by formulas (A2)-(B2) and pyridine into a third solvent, stirring for 10-15 hours, then bromopyridinium is obtained, wherein the molar ratio of the bromo ketone to pyridine is 1:0.8-2;

(II) in the atmosphere of inert gases, adding the bromopyridinium obtained in step (1), the aromatic dialdehyde represented by formula (C2), one or more of aromatic ketone represented by formulas (D2) and (E2), and catalysis amount ammonium salt, into a fourth solvent, then refluxing for 20-30 hours, the resulted crude product is purified by silicon gel chromatography column or recrystallization, wherein the molar ratio of the bromopyridinium, the aromatic dialdehyde and the aromatic ketone is (2-3):1:(2-3);

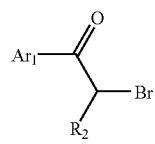

(A1)

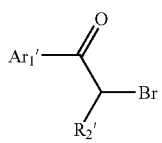

(B1)

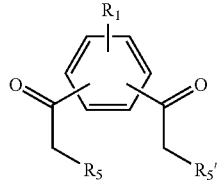

(C1)

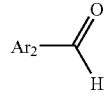

(D1)

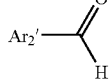

(E1)

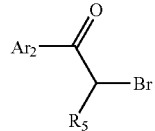

(A2)

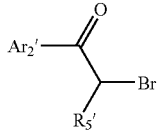

(B2)

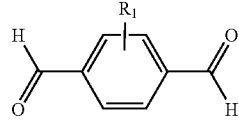

(C2)

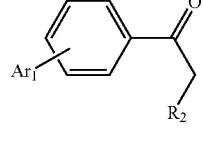

(D2)

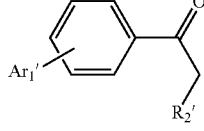

(E2)

wherein the substituents $R_1$, $R_2$, $R_2'$, $R_5$, $R_5'$, $Ar_1$, $AR_1'$, $Ar_2$, $Ar_2'$ are defined as claim 1.

According to the preparation methods of the materials provided by the present invention, said catalyst can be any ammonium carboxylate with 1-5 carbon atoms, such as ammonium formate, ammonium acetate. And the usage of the catalyst is not specially limited, for example, the amount of the catalyst can be 1-30 molar % of that of the corresponding pyridinium bromide.

Said first solvent, second solvent, third solvent and fourth solvent can be same or different and independently be acetic acid, methanol, ethanol, tetrahydrofuran, dichloromethane or dioxane.

With regard to the amount of said first solvent, second solvent, third solvent and fourth solvent, there are no special limits as long as they each can dissolve the reaction reagent to facilitate the reaction. For example, the amount of said first organic solvent can be 1-50 times (weight) of the total amount of the bromo ketone and pyridine; the amount of said second organic solvent can be 1-50 times (weight) of the total amount of the bromopyridinium, the aromatic diketone and the aromatic aldehyde, the amount of said third organic solvent can be 1-50 times (weight) of the total amount of the bromopyridinium, the bromo ketone to pyridine, and the amount of said second organic solvent can be 1-50 times (weight) of the total amount of the bromopyridinium, the aromatic dialdehyde and the aromatic ketone.

Figure 2:
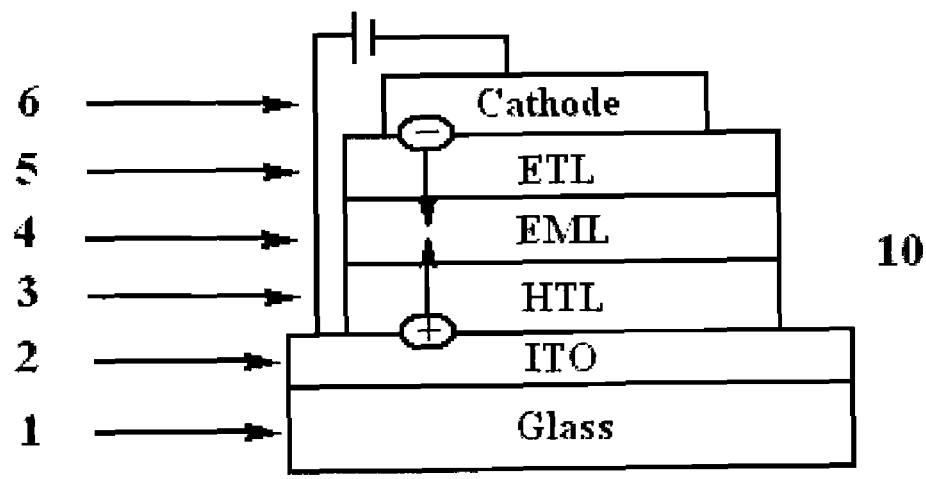
FIG. 2 illustrates a diagram of the structure of OLEDs provided by the present invention.

According to the present invention, the OLED can be any OLEDs or other organic semiconductor devices comprising ETL or requiring the performance of hole-blocking and/or electron-transporting, and said OLEDs can be such as organic semiconductor devices, doping fluorescent device, phosphorescent device, white OLEDs and so on. In one embodiment of the present invention, the OLED have the structure as shown in FIG. 1 and FIG. 2. Said other organic semiconductor devices can be such as organic transistor, organic integrated circuit, organic solar cell, organic laser or organic sensor.

Usually, the OLED have the structure as shown in FIG. 1 (see Adv. Mater. 2002 14 1317) comprising from the bottom to top, anode 2 is located on the substrate 1, HTL 3 is located on the anode 2, EML 4 is located on the HTL 3, HBL 7 is located on the EML 4, ETL is located on the HBL 7 and cathode 6 is located on the ETL 5. And an electric field is applied (external power source not shown) between the anode 2 and the cathode 6. Because the conventional electron-transporting layer comprised in the conventional OLED does not show the hole-blocking performance, the HBL 7 is necessary to the OLED.

As shown in FIG. 2, from the bottom to top, anode 2 is located on the substrate 1, HTL 3 is located on anode 2, EML 4 is located on the HTL 3, ETL 5 is located on EML 4 and cathode 6 is located on ETL 5. And an electric field is applied (external power source not shown) between anode 2 and cathode 6.

As can be seen by comparing FIG. 1 and FIG. 2, HBL 7 is necessary to the conventional OLED and be inserted into between the ETL 5 and EML 4 because the conventional electron-transporting layer 5 without the organic material having hole-blocking and/or electron-transporting performance provided by the present invention can not have high ionization potential (IP) to block the holes into EML 4 which can affect the efficiency and color purity of devices. While in the OLED provided by the present invention, the separate HBL 7 is not necessary because ETL 5 comprising the organic compound having hole-blocking and/or electron-transporting performance provided by the present invention can simultaneously function as ETL and HBL.

The substrate 1 is used as a support for the OLED of the present invention. A suitable substrate is, for example, a quartz or glass sheet, a metal sheet or foil, or a plastic film or sheet. The preferred material for using in the device is a glass sheet, or a transparent synthetic resin, such as a polyester, polycarbonate, or polysulfone.

An anode 2 is located on the substrate 1. It is usually made of a metal such as silver, gold, aluminum, nickel, palladium, a metal oxide such as an oxide of indium and/or tin, e.g., indium tin oxide (ITO), carbon black, or a conductive resin such as poly(3-methylthiophene). The materials mentioned above for preparing anode 2 may also be employed in preparing cathode 6. However, the preferred material for cathode 6 is a metal with low work function, which is conducive to the efficient injection of electrons. Thus, a suitable metal such as magnesium, aluminum, silver, indium, or their alloys may be used.

Methods for preparing anode 2 and cathode 6 generally include vacuum deposition and sputtering. However, when the material comprises fine particles of metal, carbon black, metal oxide, or conductive resin powder, it can be dispersed into a suitable binder resin in solution and coated on a substrate to form the electrodes. Furthermore, in the case of a conductive resin, a thin film may be formed directly on a substrate by electrolytic polymerization.

Anode 2 and/or cathode 6 can be made to have a multi-layered structure by depositing to form layers of the different materials mentioned above. However, at least one of the electrodes should be able to transmit visible light to a required degree which is usually at least 60%, but preferably at least 80%. In this respect, the layer should not be too thick, generally from 5-1,000 nm, and preferably from 10-500 nm.

An organic hole-transporting layer 3 is located on anode 2. It generally comprises a compound that is able to transport holes (i.e. positive charge carriers) efficiently from anode 2 to the organic emitting layer 4 between the electrodes to which an electric field is applied (external power source not shown). Such a compound must be highly efficient at injecting holes from the anode. In addition, the compound must be capable of efficiently transporting the injected holes to an emitting material found in emitting layer 4, thereby preventing the migration of excitons generated in emitting layer 4 from an electron injecting zone or an electron-transporting material. The material should also be highly capable of forming a thin film. Thus, in this respect, a suitable hole-transporting compound usually has a low ionization potential, large hole mobility and stability. Moreover, the impurities likely to form traps should not be produced during preparation or use. In the present invention N,N'-bis-(1-naphthyl)-N,N'-diphenylbenzidine (NPB) is used as HTL.

The hole transporting material can be laminated on anode 2 by a vacuum deposition method or a coating/casting method to form organic hole transporting layer (HTL) 3 in the present invention. This hole transporting layer usually has a thickness of 5-400 nm, preferably 30-100 nm. In order to obtain a thin film uniformly, the vacuum deposition method is preferred.

The organic electron-transporting layer (ETL) 5 should comprise a material into which electrons from cathode 6 can be injected easily, which has excellent electron transport mobility, and which blocks the migration of excitons generated in the EML 4 into the hole injection zone. Moreover, a material which has a good ability to form a thin film is desirable. Useful electron transport materials generally have a large electron affinity. According to the present invention, the ETL5 is wholly or mainly composed of the compound having electron-transporting and/or hole-blocking performance provided by the present invention.

ETL 5 can be formed by a vacuum deposition method or a coating/casting method. This electron-transporting layer 5 usually has a thickness of 5-400 nm, preferably 30-100 nm. In order to obtain a thin film uniformly, vacuum deposition is preferred.

The light emitting material forming the EML 4 of OLEDs is generally required to have a high emission quantum yield, a suitable energy gap, as well as a good ability to form a thin film uniformly and electroluminescence is the result of electron-hole recombination in this region. This electron-hole recombination produces excitons, which may decay to the ground state in a radiation way, resulting in an emission-fluorescence or phosphorescence. The conventionally used light emitting material is one or more of fused aromatic compounds, benzidine type triphenylamine, styrylamine type triphenylamine, diamine type triphenylamine, 8-hydroxyquinolinato metal complexes, such as AlQ3, as well as other fluorescence or phosphorescence dyes.

As previously mentioned, doping a strong luminescent material into one of the light emitting materials (host) mentioned above can significantly improve the performance of an OLED. Accordingly, in the present invention, the EML 4 of the OLED provided by the present invention preferably further comprises a multi-component material containing one or more of the novel organic compound having hole-blocking and/or electron-transporting performance provided by the present invention as a dopant (guest). The concentration of the dopant can be 1-10 wt % of that of the host material.

According to one embodiment of the present invention, the organic electroluminescence device (OLED) provided by the invention can be fabricated by the following methods.

A glass substrate 1 coated with indium-tin-dioxide (ITO) as anode 2 was sequentially ultrasonicated in a detergent to remove the dust on the surface of the glass substrate 1, rinsed in deionized water to remove the rudimental detergent and exposed to UV light for 20 minutes, and dried. A hole transporting layer 3 of N,N'-bis-(1-naphthyl)-N,N'-diphenylbenzidine (NPB) was deposited on ITO anode 2 at the vacuum deposition rate of about 15 nm/min by using a tantalum boat to form a thickness of 60 nm. A emitting layer 4 was then deposited onto the hole-transporting layer 3 with a thickness of about 30 nm. The emitting layer 4 comprises green material tris(8-hydroxyquinoline)aluminum(Alq3), blue material 9,10-di(2-naphthyl)anthracene (ADN), or red material rubrene and so on as dopants, and one or more the novel organic material having hole-blocking and/or electron-transporting performance provided by the present invention as a host emitting material. The concentration of dopants can be controlled by deposition rate as required. In the following step, an electron-transporting layer 5 of the new material selected from one or more of the formulas (a)-(l) was deposited onto the emitting layer 4 with a thickness of about 30 nm at the vacuum deposition rate of about 0.1 nm/sec. Then, a cathode 6 consisting of a 10/1 atomic ratio of Mg/Ag was deposited onto the ETL 5 with a thickness of about 100 nm. Finally, the device was obtained as shown in FIG. 1 and hermetically packaged in a dry glove box.

In order to demonstrate the hole-blocking ability of the novel materials provided by the present invention, we design another device structured with: Anode2/HTL3/EML4/HBL7/ETL5/Cathode6 as shown in FIG. 1, which differs from the conventional OLED in that HBL 7 is made of the compound provided by the present invention, other electron-transporting materials, for example tris(8-hydroxyquinoline)aluminum(Alq3), 4,7-diphenyl-1,10-phenanthroline(BPhen) and so on as ETL. The efficiency and color purity of devices are also improved heavily. The method of depositing ETL and device fabricating are as same as that of the conventional OLED.

EXAMPLES

The present invention will be explained in more detail with reference to examples hereinafter. It should be noted that the examples included below are for illustrative purposes only, and that the invention is in no way limited to the embodiments used in the examples.

Unless otherwise indicated, the reactants and reagents used in the reactions described below are readily available materials. The reagents which comprises atom bromine can be conveniently prepared in accordance with conventional preparatory procedures (for example see Synthesis Krohnke F 1976(01) P1 The specific synthesis of pyridines and oligopridines). The others were all obtained from commercial sources (Acros Organics). In addition, the characteristics of the devices were measured using a Spectrascan PR650 photometer and a computer-controlled Keithley 2400 SourceMeter under ambient atmosphere. And in the following examples, 1 wt % TBP:ADN means 1 weight part of TBP(2,5,8,11-tetra-tertbutylperylene) as dopant is mixed with 99 weight parts of ADN (9,10-di(2-naphthyl)anthracene), 6 wt % FIrpic:CBP means 6 weight part of FIrpic (Bis(4,6-difluorophenylpyridinato-N,C2)picolinatoiridium) as dopant is mixed with 99 weight parts of CBP (4,4'-Bis-(carbazol-9-yl)biphenyl), 5 wt % DSA-Ph:MADNmeans 5 weight part of DSA-Ph (bis[4-(di-p-N,N-diphenylamino)styryl]stilbene) as dopant is mixed with 99 weight parts of MADN (2-methyl-9,10-di(2-naphthyl)anthracene). In all following examples, the reaction of preparing pyridinium bromide is carried out in the nitrogen atmosphere.

Example 1

Synthesis of 1,4-bis(4,6-diphenyl-5-(trifluoromethyl)pyridin-2-yl)benzene(BDTPB)

2-bromo-3,3,3-trifluoro-1-phenylpropan-1-one and pyridine (1:1 in molar ratio) were stirred at the room temperature of 25° C. for 10 hours in ethanol (2 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, 1,4-diacetylbenzene and benzaldehyde (2:1:2 in molar ratio) were added into a three-necked flask and then acetic acid (5 times (weight) of the total amount of the resulted pyridinium bromide, 1,4-diacetylbenzene and benzaldehyde) and catalysis amount ammonium acetate (10 molar % of the resulted pyridinium bromide) (10 molar % of the resulted pyridinium bromide) were added therein. The mixtures were refluxed for 24 hours, then crude product was obtained. Finally the multi-aryl substituted pyridine derivative was obtained via silicon gel chromatography column with $CH_2Cl_2$/Petroleum ether(3:1 v/v) as the eluent. The yield was about 50%.

m/z: 672.20 (100.0%), 673.20 (46.2%), 674.21 (10.2%), 675.21 (1.5%)

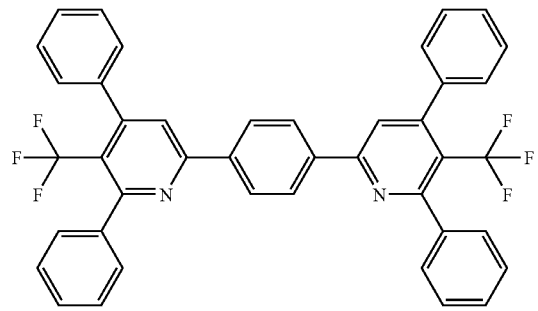

OLED device using BDTPB as HBL
Device Structure as FIG. 1:
ITO/NPB(75 nm)/ADN:TBP(30 nm)/BDTPB(5 nm)/BPhen(30 nm)/LiF(0.5 n m)/MgAg(100 nm)
CIE Coordinate: X=0.15, Y=0.22
Turn-on Voltage: 4.2V
Maximal Brightness: 19800 cd/m$^2$ (12V)
Current Efficiency: 5.5 cd/A Example 2

Synthesis of 1,4-bis(6-phenyl-4-p-tolyl-5-(trifluoromethyl)pyridin-2-yl)benzene (BPTTPB I)

2-bromo-3,3,3-trifluoro-1-phenylpropan-1-one and pyridine (1:2 in molar ratio) were stirred at 40° C. for 11 hours in methanol (5 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, 1,4-diacetylbenzene and p-methylbenzaldehyde (3:1;3 in molar ratio) were added into a three-necked flask, and then acetic acid resulted pyridinium bromide, 1,4-diacetylbenzene and benzaldehyde and catalysis amount ammonium formate (10 molar % of the resulted pyridinium bromide) (10 molar % of the resulted pyridinium bromide) were added therein. The mixtures were refluxed for 30 hours, then crude product was obtained. Finally the multi-aryl substituted pyridine derivatives was obtained via silicon gel chromatography column with $CH_2Cl_2$/Petroleum ether (3:1 v/v) as the eluent. The yield was about 55%.

m/z: 700.23 (100.0%), 701.23 (48.3%), 702.24 (11.2%), 703.24 (1.8%)

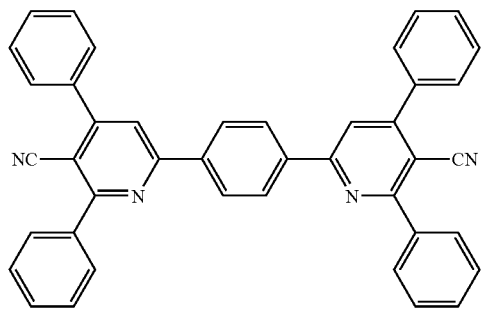

OLED device using compound PBDNN as ETL
Device structure as FIG. 2:
ITO/NPB(75 nm)/ADN:TBP(30 nm)/PBDNN(35 nm)/LiF(0.5 nm)/MgAg(100 nm)
CIE coordinate: X=0.15, Y=0.22
Turn-on voltage: 4.2V
Maximal brightness: 19500 cd/m$^2$ (12V)
Current efficiency: 5.2 cd/A Example 4

Synthesis of 6,6'-(1,4-phenylene) bis(4-(4-tert-butylphenyl)-2-phenylnicotinonitrile) (PBBPNN)

2-bromo-3-oxo-3-phenylpropanenitrile and pyridine (1:0.8 in molar ratio) were stirred at 10° C. for 12 hours in ethanol (50 times (weight) of the total amount of 2-bromo-3-oxo-3-phenylpropanenitrile and pyridine), then filtrated, and the resulted solids were washed with water, pyridinium bromide was obtained.

The resulted pyridinium bromide, 1,4-diacetylbenzene and 4-tert-butylbenzaldehyde (2:1:2.5 in molar ratio) were added into a three-necked flask. And then dioxane (50 times (weight) of the total amount of the resulted pyridinium bromide, 1,4-diacetylbenzene and 4-tert-butylbenzaldehyde) and catalysis amount ammonium formate (10 molar % of the resulted pyridinium bromide) (20 molar % of the resulted pyridinium bromide) were added therein. The mixtures were refluxed for 25 hours, then crude product was obtained. Finally the multi-aryl substituted pyridine derivatives were obtained via recrystallization with o-dichlorobenzene. The yield was about 50%.

m/z: 698.34 (100.0%), 699.34 (55.6%), 700.35 (14.6%), 701.35 (2.6%)

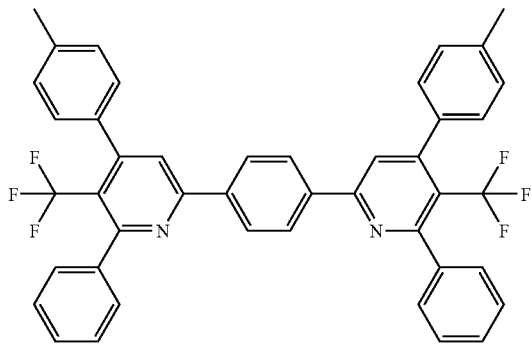

OLED device using BPTTPB I as HBL
Device Structure as FIG. 1:
ITO/NPB(75 nm)/ADN:TBP(30 nm)/BPTTPB I (5 nm)/BPhen(30 nm)/LiF(0.5 nm)/MgAg(100 nm)
CIE Coordinate: X=0.15, Y=0.22
Turn-on Voltage: 4.2V
Maximal Brightness: 19800 cd/m$^2$ (12V)
Current Efficiency: 5.5 cd/A Example 3

Synthesis of 6,6'-(1,4-phenylene)bis(2,4-diphenylnicotinonitrile) (PBDNN)

2-bromo-3-oxo-3-phenylpropanenitrile and pyridine (1:1.5 in molar ratio) were stirred at −5° C. for 10 hours in dichloromethane (10 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, 1,4-diacetylbenzene and benzaldehyde (2.5:1:2 in molar ratio) were added into a three-necked flask. And then tetrahydrofuran (20 times (weight) of the total amount of the resulted pyridinium bromide, 1,4-diacetylbenzene and benzaldehyde) and catalysis amount ammonium acetate (10 molar % of the resulted pyridinium bromide) (30 molar % of the resulted pyridinium bromide) were added therein. The mixtures were refluxed for 24 hours, then crude product was obtained. Finally the multi-aryl substituted pyridine derivative was obtained via recrystallization with o-dichlorobenzene. The yield was about 50%.

m/z: 586.22 (100.0%), 587.22 (45.7%), 588.22 (10.7%), 589.23 (1.5%), 587.21 (1.5%)

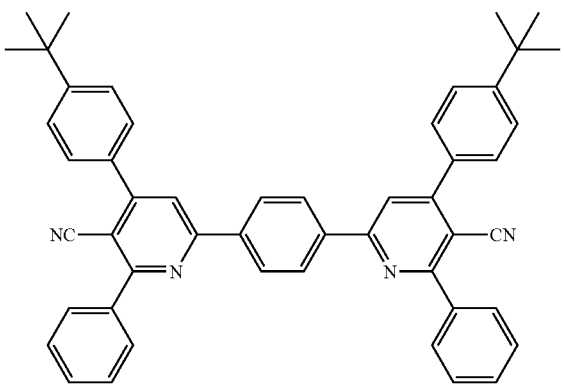

OLED device using compound PBBPNN as ETL
Device structure as FIG. 2:
ITO/NPB(75 nm)/ADN(30 nm)/PBBPNN(35 nm)/LiF (0.5 nm)/MgAg(100 nm)
CIE coordinate: X=0.15, Y=0.08
Turn-on voltage: 4.2V
Maximal brightness: 19800 cd/m$^2$ (12V)
Current efficiency: 4.5 cd/A Example 5

Synthesis of diethyl 6,6'-(1,4-phenylene) bis(2-phenyl-4-p-tolylnicotinate) (PBPTNN I)

Ethyl 2-bromo-3-oxo-3-phenylpropanoate and pyridine (1:1 in molar ratio) were stirred at 25° C. for 15 hours in methanol (20 times (weight) of the total amount of ethyl 2-bromo-3-oxo-3-phenylpropanoate and pyridine), then filtrated, and the solids were washed with water, thereby pyridinium bromide was obtained.

The resulted pyridinium bromide, 1,4-diacetylbenzene and 4-methylbenzaldehyde (2.5:1:2.5 in molar ratio) were added into a three-necked flask. And then acetic acid (20 times (weight) of the total amount of the resulted pyridinium bromide, 1,4-diacetylbenzene and 4-methylbenzaldehyde) and catalysis amount ammonium acetate (10 molar % of the resulted pyridinium bromide) (15 molar % of the resulted pyridinium bromide) were added therein. The mixtures were refluxed for 23 hours, then crude product was obtained. Finally the multi-aryl substituted pyridine derivative was obtained via silicon gel chromatography column with CH$_2$Cl$_2$/Petroleum ether (3:1 v/v) as the eluent. The yield was about 60%.

m/z: 708.30 (100.0%), 709.30 (52.8%), 710.31 (13.5%), 711.31 (2.7%), 710.30 (1.2%)

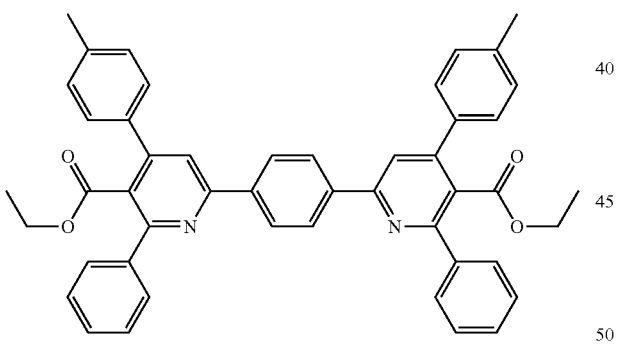

OLED device using compound PBPTNN I as HBL
Device Structure as FIG. 1:
ITO/NPB(75 nm)/ADN:TBP(30 nm)/PBPTNN I (5 nm)/Alq3(30 nm)/LiF(0.5 nm)/MgAg(100 nm)
CIE coordinate: X=0.15, Y=0.2
Turn-on voltage: 3.8V
Maximal brightness: 19000 cd/m$^2$ (12V)
Current efficiency: 5.6 cd/A Example 6

Synthesis of 6,6'-(1,4-phenylene)bis(2,4-diphenylpyridine-3,5-dicarbonitrile) (PBDPD)

2-bromo-3-oxo-3-phenylpropanenitrile and pyridine (1:1 in molar ratio) were stirred at 25° C. for 14 hours in dichloromethane (20 times (weight) of the total amount of 2-bromo-3-oxo-3-phenylpropanenitrile and pyridine), then filtrated, and the solids were washed with water, thereby pyridinium bromide was obtained.

The resulted pyridinium bromide, 3,3'-(1,4-phenylene) bis (3-oxopropanenitrile) and benzaldehyde (2:1:2 in molar ratio) were added into a three-necked flask. And then tetrahydrofuran (20 times (weight) of the total amount of the resulted pyridinium bromide, 3,3'-(1,4-phenylene) bis(3-oxopropanenitrile) and benzaldehyde) and catalysis amount ammonium formate (10 molar % of the resulted pyridinium bromide) (10 molar % of the resulted pyridinium bromide) were added therein. The mixtures were refluxed for 27 hours, then crude product was obtained. Finally the multi-aryl substituted pyridine derivative was obtained via silicon gel chromatography column with CH$_2$Cl$_2$/Petroleum ether(3:1 v/v). The yield was about 45%.

m/z: 636.21 (100.0%), 637.21 (47.9%), 638.21 (12.1%), 637.20 (2.2%), 639.22 (1.7%)

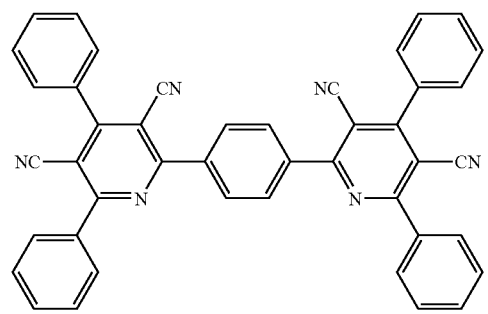

OLED device using compound PBDPD as ETL
Device structure as FIG. 2:
ITO/NPB(75 nm)/ADN:TBP(30 nm)/PBDPD(35 nm)/LiF (0.5 nm)/MgAg(100 nm)
CIE coordinate: X=0.15, Y=0.2
Turn-on voltage: 3.8V
Maximal brightness: 19000 cd/m$^2$ (12V)
Current efficiency: 5.6 cd/A Example 7

Synthesis of 6,6'-(1,4-phenylene) bis(4-(4-tert-butylphenyl)-2-phenylpridine-3,5-dicarbonitrile) (PBBPD I)

2-bromo-3-oxo-3-phenylpropanenitrile and pyridine (1:1 in molar ratio) were stirred at 25° C.
for 13 hours in ethanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide,
3,3'-(1,4-phenylene)bis(3-oxopropanenitrile) and p-butylbenzaldehyde (2:1:2 in molar ratio) were added into a three-necked flask. And then acetic acid (20 times (weight) of the total amount of the resulted pyridinium bromide, 3,3'-(1,4-phenylene)bis(3-oxopropanenitrile) and p-butylbenzaldehyde) and catalysis amount ammonium acetate (10 molar % of the resulted pyridinium bromide) (10 molar % of the resulted pyridinium bromide) were added therein. The mixtures were refluxed for 26 hours, then crude product was obtained. Finally the multi-aryl substituted pyridine derivative was obtained via recrystallization with o-dichlorobenzene. The yield was about 50%.

m/z: 748.33 (100.0%), 749.33 (58.5%), 750.34 (15.8%), 751.34 (3.2%), 750.33 (1.3%)

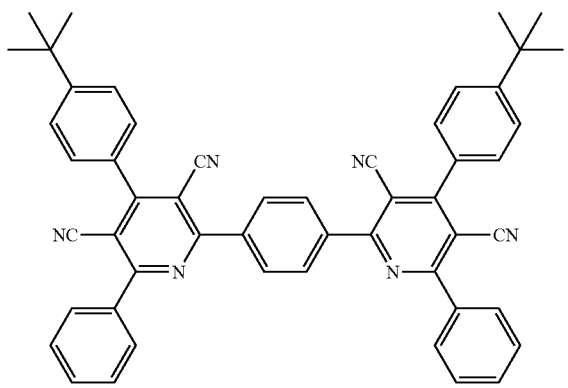

OLED device using compound PBBPD I as HBL
Device structure as FIG. 1:
ITO/NPB(75 nm)/ADN:TBP(30 nm)/PBBPD I (5 nm)/BPhen(30 nm)/LiF(0.5 nm)/MgAg(100 nm)
CIE coordinate: X=0.15, Y=0.2
Turn-on voltage: 3.8V
Maximal brightness: 19000 cd/m$^2$ (12V)
Current efficiency: 5.6 cd/A Example 8

Synthesis of 1,4-bis(4-(furan-2-yl)-6-phenyl-5-(trifluoromethyl)pyridin-2-yl)benzene (BFPTPB I)

2-bromo-3,3,3-trifluoro-1-phenylpropan-1-one and pyridine (1:1 in molar ratio) were stirred at 25° C. for 11 hours in methanol (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, 1,4-diacetylbenzene and furan-2-carbaldehyde (2:1:2 in molar ratio) were added into a three-necked flask. And then dioxane (20 times (weight) of the total amount of the resulted pyridinium bromide, 1,4-diacetylbenzene and furan-2-carbaldehyde) and ammonium acetate (10 molar % of the resulted pyridinium bromide) were added therein. The mixtures were refluxed for 23 hours, then crude product was obtained. Finally the multi-aryl substituted pyridine derivative was obtained via crystallization with o-dichlorobenzene. The yield was about 48%.
m/z: 652.16 (100.0%), 653.16 (42.2%), 654.17 (8.4%), 655.17 (1.3%)

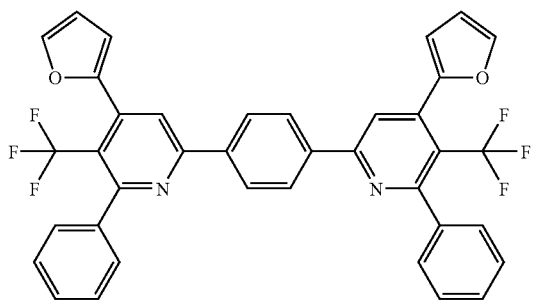

OLED device using compound BFPTPB I as ETL
Device structure as FIG. 2:
ITO/NPB(75 nm)/ADN:TBP(30 nm)/BFPTPB I (35 nm)/LiF(0.5 nm)/MgAg(100 nm)
CIE coordinate: X=0.15, Y=0.22
Turn-on voltage: 3.9V
Maximal brightness: 19000 cd/m$^2$ (12V)
Current efficiency: 5.0 cd/A Example 9

Synthesis of 1,3-bis(6-phenyl-4-p-tolyl-5-(trifluoromethyl)-pyridin-2-yl)benzene (BPTPB I)

2-bromo-3,3,3-trifluoro-1-phenylpropan-1-one and pyridine (1:1 in molar ratio) were stirred at 25° C. for 15 hours in dichloromethane (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, 1,3-diacetylbenzene and 4-methylbenzaldehyde (2:1:2 in molar ratio) were added into a three-necked flask. And then tetrahydrofuran (20 times (weight) of the total amount of the resulted pyridinium bromide, 1,3-diacetylbenzene and 4-methylbenzaldehyde) and catalysis amount of ammonium acetate (10 molar % of the resulted pyridinium bromide) were added therein. The mixtures were refluxed for 22 hours, then crude product was obtained. Finally the multi-aryl substituted pyridine derivative was obtained via silicon gel chromatography column with CH$_2$Cl$_2$/Petroleum ether(3:1 v/v) as the eluent. The yield was about 60%.
m/z: 700.23 (100.0%), 701.23 (48.3%), 702.24 (11.2%), 703.24 (1.8%)

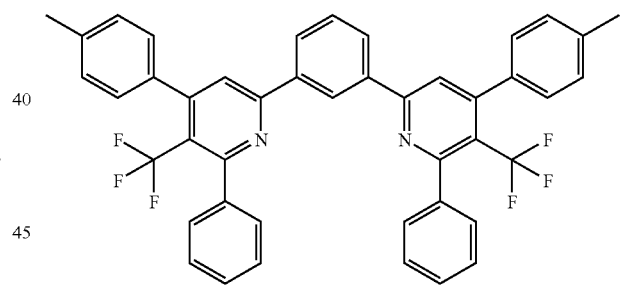

OLED device using compound BPTPB I as HBL
Device structure as FIG. 1:
ITO/NPB(75 nm)/ADN:TBP(30 nm)/BPTPB I (5 nm)/Alq3(30 nm)/LiF(0.5 nm)/MgAg(100 nm)
CIE coordinate: X=0.15, Y=0.22
Turn-on voltage: 3.9V
Maximal brightness: 19000 cd/m$^2$ (12V)
Current efficiency: 5.0 cd/A Example 10

Synthesis of 1,3-bis(4-(4-methoxyphenyl)-6-phenyl-5-(trifluoromethyl)pyridin-2-yl)benzene (BMPTPB I)

2-bromo-3,3,3-trifluoro-1-phenylpropan-1-one and pyridine (1:1 in molar ratio) were stirred at 25° C. for 13 hours in ethanol (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, 1,3-diacetylbenzene and 4-methoxybenzaldehyde (2:1:2 in molar ratio) were added into a three-necked flask. And then dioxane (20 times (weight) of the total amount of the resulted pyridinium bromide, 1,3-diacetylbenzene and 4-methoxybenzaldehyde) and catalysis amount ammonium acetate (10 molar % of the resulted pyridinium bromide) were added therein. The mixtures were refluxed for 20 hours, then crude product was obtained. Finally the multi-aryl substituted pyridine derivative was obtained via silicon gel chromatography column with $CH_2Cl_2$/Petroleum ether(3:1 v/v) as the eluent. The yield was about 55%.

m/z: 732.22 (100.0%), 733.22 (48.3%), 734.23 (11.7%), 735.23 (1.9%)

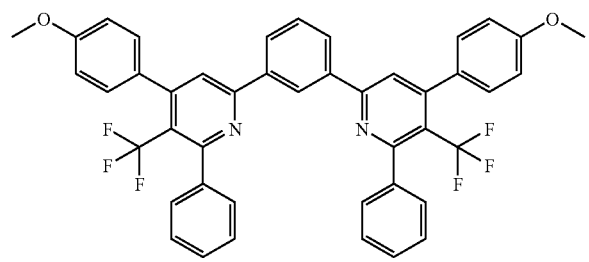

OLED device using compound BMPTPB I as ETL
Device structure as FIG. 2:
ITO/NPB(75 nm)/ADN:TBP(30 nm)/BMPTPB I (35 nm)/LiF(0.5 nm)/MgAg(100 nm)
CIE coordinate: X=0.15, Y=0.22
Turn-on voltage: 4.0V
Maximal brightness: 19800 cd/m$^2$ (12V)
Current efficiency: 5.4 cd/A Example 11

Synthesis of 6,6'-(1,3-phenylene) bis(2-phenyl-4-p-tolylnicotinonitrile) (PBTNN I)

2-bromo-3-oxo-3-phenylpropanenitrile and pyridine (1:1 in molar ratio)were stirred at 25° C. for 13 hours in methanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, 1,3-diacetylbenzene and 4-methylbenzaldehyde (2:1:2 in molar ratio) were added into a three-necked flask. And then acetic acid (20 times (weight) of the total amount of the resulted pyridinium bromide, 1,3-diacetylbenzene and 4-methylbenzaldehyde) and catalysis amount ammonium acetate (10 molar % of the resulted pyridinium bromide) were added therein. The mixtures were refluxed for 26 hours, then crude product was obtained. Finally the multi-aryl substituted pyridine derivative was obtained via recrystallization with o-dichlorobenzene. The yield was about 45%.

m/z: 614.25 (100.0%), 615.25 (47.9%), 616.25 (11.8%), 617.26 (1.7%), 615.24 (1.5%)

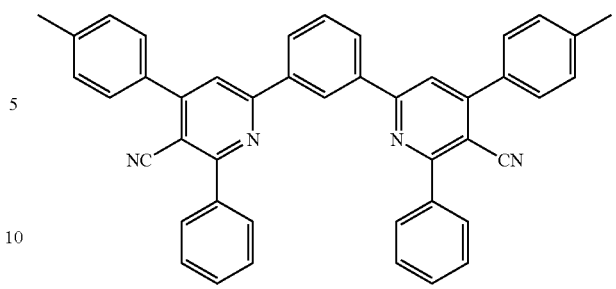

OLED device using compound PBTNN I as ETL
Device structure as FIG. 2:
ITO/NPB(75 nm)/ADN:TBP(30 nm)/PBTNN I (35 nm)/LiF(0.5 nm)/MgAg(100 nm)
CIE coordinate: X=0.15, Y=0.22
Turn-on voltage: 5.2V
Maximal brightness: 19800 cd/m$^2$ (12V)
Current efficiency: 4.5 cd/A Example 12

Synthesis of 6,6'-(1,3-phenylene) bis(4-(4-tert-butylphenyl)-2-phenylnicotinonitrile) (PBTPNN I)

2-bromo-3-oxo-3-phenylpropanenitrile and pyridine (1:1 in molar ratio)were stirred at 25° C. for 14 hours in dichloramethane (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, 1,3-diacetylbenzene and 4-butylbenzaldehyde (2:1:2 in molar ratio) were added into a three-necked flask. And then tetrahydrofuran (20 times (weight) of the total amount of the resulted pyridinium bromide, 1,3-diacetylbenzene and 4-butylbenzaldehyde) and catalysis amount ammonium acetate (10 molar % of the resulted pyridinium bromide) were added therein. The mixtures were refluxed for 25 hours, then crude product was obtained. Finally the multi-aryl substituted pyridine derivative was obtained via recrystallization with o-dichlorobenene. The yield was about 55%.

m/z: 698.34 (100.0%), 699.34 (55.6%), 700.35 (14.6%), 701.35 (2.6%)

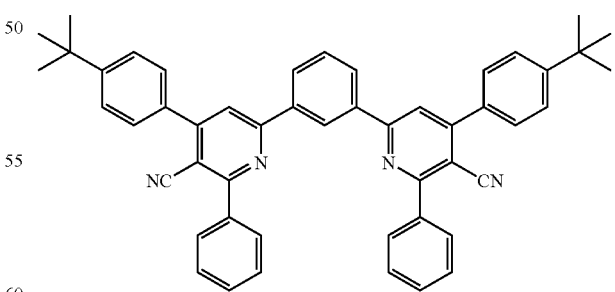

OLED device using compound PBTPNN I as HBL
Device structure as FIG. 1:
ITO/NPB(75 nm)/ADN:TBP(30 nm)/PBTPNN I (5 nm)/Alq3(30 nm)/LiF(0.5 nm)/MgAg(100 nm)
CIE coordinate: X=0.15, Y=0.22
Turn-on voltage: 4.2V Maximal brightness: 19800 cd/m² (12V)
Current efficiency: 5.5 cd/A

Example 13

Synthesis of diethyl 6,6'-(1,3-phenylene)bis(4-(4-methoxyphenyl)-2-phenylnicotinate) (PBMPNN I)

Ethyl 2-bromo-3-oxo-3-phenylpropanoate and pyridine (1:1 in molar ratio) were stirred at 25° C. for 11 hours in ethanol (20 times (weight) of the total amount of ethyl 2-bromo-3-oxo-3-phenylpropanoate and pyridine), then filtrated, and the resulted solids were washed with water, thereby pyridinium bromide was obtained.

The resulted pyridinium bromide, 1,3-diacetylbenzene and 4-methoxybenzaldehyde (2:1:2 in molar ratio) were added into a three-necked flask. And then acetic acid (20 times (weight) of the total amount of the resulted pyridinium bromide, 1,3-diacetylbenzene and 4-methoxybenzaldehyde) and catalysis amount ammonium acetate (10 molar % of the resulted pyridinium bromide) were added therein. The mixtures were refluxed for 23 hours, then crude product was obtained. Finally the multi-aryl substituted pyridine derivative was obtained via silicon gel chromatography column with CH$_2$Cl$_2$/Petroleum ether(3:1 v/v) as the eluent. The yield was about 60%.

m/z: 740.29 (100.0%), 741.29 (53.3%), 742.30 (13.6%), 743.30 (2.9%), 742.29 (1.6%)

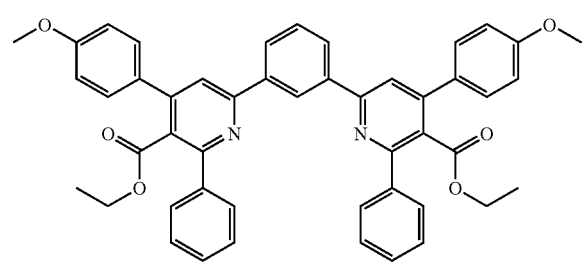

OLED device using compound PBMPNN I as ETL
Device structure as FIG. 2:
ITO/NPB(75 nm)/ADN (30 nm)/PBMPNN I (35 nm)/LiF (0.5 nm)/MgAg(100 nm)
CIE coordinate: X=0.15, Y=0.09
Turn-on voltage: 3.9V
Maximal brightness: 20000 cd/m² (12V)
Current efficiency: 4.6 cd/A

Example 14

Synthesis of 1,3-bis(6-phenyl-4-p-tolyl-3,5-bis(trifluoromethyl)pyridine-2-yl)benzene (PTTPBN)

2-bromo-3,3,3-trifluoro-1-phenylpropan-1-one and pyridine (1:1 in molar ratio) were stirred at 25° C. for 10 hours in methanol (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, 1,1'-(1,4-phenylene)bis (3,3,3-trifluoropropan-1-one) and 4-methylbenzaldehyde (2:1:2 in molar ratio) were added into a three-necked flask. And then dioxane (20 times (weight) of the total amount of the resulted pyridinium bromide, 1,1'-(1,4-phenylene)bis(3,3,3-trifluoropropan-1-one) and 4-methylbenzaldehyde) and catalysis amount ammonium formate (10 molar % of the resulted pyridinium bromide) were added therein. The mixtures were refluxed for 21 hours, then crude product was obtained. Finally the multi-aryl substituted pyridine derivative was obtained via silicon gel chromatography column with CH$_2$Cl$_2$/Petroleum ether(3:1 v/v) as the eluent. The yield was about 60%.

m/z: 722.19 (100.0%), 723.19 (49.1%), 724.20 (11.2%), 725.20 (1.7%)

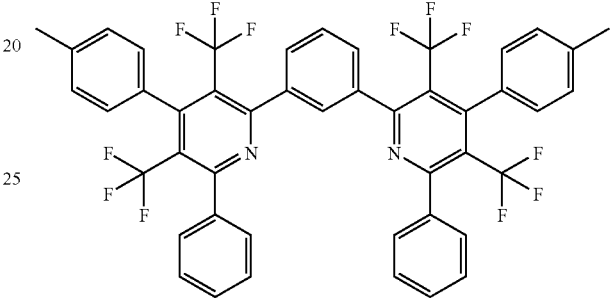

OLED device using compound PTTPBN as ETL
Device structure as FIG. 2:
ITO/NPB(75 nm)/ADN:TBP(30 nm)/PTTPBN (35 nm)/LiF(0.5 nm)/MgAg(100 nm)
CIE coordinate: X=0.15, Y=0.22
Turn-on voltage: 4.4V
Maximal brightness: 20020 cd/m² (12V)
Current efficiency: 5.2 cd/A

Example 15

Synthesis of 6,6'-(1,3-phenylene) bis(4-(4-tert-butylphenyl)-2-phenylpyridin-3,5-dicarbonitrile) (PB-PPD I)

2-bromo-3-oxo-3-phenylpropanenitrile and pyridine (1:2 in molar ratio) were stirred at 25° C. for 11 hours in dichloromethane (20 times (weight) of the total amount of 2-bromo-3-oxo-3-phenylpropanenitrile and pyridine), then filtrated, and the resulted solids were washed with water, pyridinium bromide was obtained.

The resulted pyridinium bromide, 3,3'-(1,3-phenylene)bis (3-oxopropanenitrile) and 4-tert-butylbenzaldehyde (2:1:2 in molar ratio) were added into a three-necked flask. And then tetrahydrofuran (20 times (weight) of the total amount of the resulted pyridinium bromide, 3,3'-(1,3-phenylene)bis(3-oxopropanenitrile) and 4-tert-butylbenzaldehyde) and a little ammonium acetate (10 molar % of the resulted pyridinium bromide) for catalysis were added therein. The mixtures were refluxed for 20 hours, then crude product was obtained. Finally the multi-aryl substituted pyridine derivative was obtained via recrystallization with o-dichlorobenzene. The yield was about 45%.

m/z: 748.33 (100.0%), 749.33 (58.5%), 750.34 (15.8%), 751.34 (3.2%), 750.33 (1.3%)

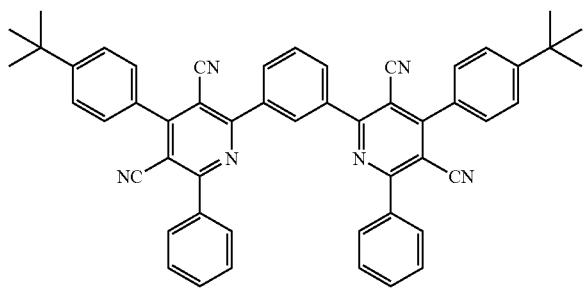

OLED device using compound PBPPD I as ETL
Device structure as FIG. 2:
ITO/NPB (30 nm)/6 wt % FIrpic:CBP(30 nm)/PBPPD I (30 nm)/LiF(0.5)/Al(100 nm)
CIE coordinate: X=0.15, Y=0.22
Turn-on voltage: 3.8V
Maximal brightness: 19800 cd/m$^2$ (12V)
Current efficiency: 11 cd/A Example 16

Synthesis of 1,3-bis(4-(furan-3-yl)-6-phenyl-5-(trifluoromethyl)pyridin-2-yl)benzene (BFPTPB)

2-bromo-3,3,3-trifluoro-1-phenylpropan-1-one and pyridine (1:2 in molar ratio) were stirred at 25° C. for 11 hours in ethanol (20 times (weight) of the total amount of 2-bromo-3,3,3-trifluoro-1-phenylpropan-1-one), then filtrated, the resulted solids were washed with water, pyridinium bromide was obtained.

The resulted pyridinium bromide, 1,3-diacetylbenzene and furan-3-carbaldehyde (3:1:3 in molar ratio) were added into a three-necked flask. And then dioxane (20 times (weight) of the total amount of the resulted pyridinium bromide, 1,3-diacetylbenzene and furan-3-carbaldehyde) and catalysis amount ammonium acetate (10 molar % of the resulted pyridinium bromide) were added therein. The mixtures were refluxed for 24 hours, then crude product was obtained. Finally the multi-aryl substituted pyridine derivative was obtained via recrystallization with o-dichlorobenzene. The yield was about 50%.

m/z: 652.16 (100.0%), 653.16 (42.2%), 654.17 (8.4%), 655.17 (1.3%)

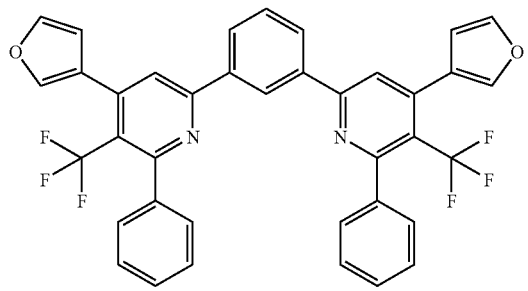

OLED device using compound BFPTPB as ETL
Device structure as FIG. 2:
ITO/NPB (30 nm)/6 wt % FIrpic: CBP (30 nm)/BFPTPB (30 nm)/LiF(0.5)/Al(100 nm)
CIE coordinate: X=0.15, Y=0.22
Turn-on voltage: 3.8V
Maximal brightness: 19800 cd/m$^2$ (12V)
Current efficiency: 11 cd/A Example 17

Synthesis of 1,2-bis(4-(4-methoxyphenyl)-6-phenyl-5-(trifluoromethyl)pyridin-2-yl)benzene (PPTPB)

2-bromo-3,3,3-trifluoro-1-phenylpropan-1-one and pyridine (1:1 in molar ratio) were stirred at room temperature for 14 hours in methanol (20 times (weight) of the total amount of 2-bromo-3,3,3-trifluoro-1-phenylpropan-1-one and pyridine), then filtrate, washed with water, pyridinium bromide was obtained.

The resulted pyridinium bromide, 1,2-diacetylbenzene and 4-methoxybenzaldehyde (3:1:3 in molar ratio) were added into a three-necked flask. And then acetic acid (20 times (weight) of the total amount of the resulted pyridinium bromide, 1,2-diacetylbenzene and 4-methoxybenzaldehyde) and catalysis amount ammonium acetate (10 molar % of the resulted pyridinium bromide) were added therein. The mixtures were refluxed for 24 hours, then crude product was obtained. Finally the multi-aryl substituted pyridine derivative was obtained via silicon gel chromatography column with CH$_2$Cl$_2$/Petroleum ether(3:1 v/v) as the eluent. The yield was about 55%.

m/z: 732.22 (100.0%), 733.22 (48.3%), 734.23 (11.7%), 735.23 (1.9%).

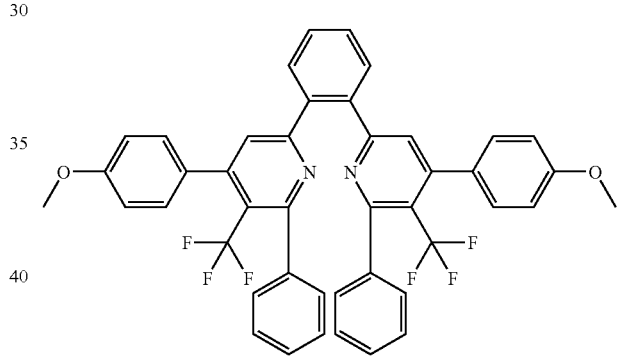

OLED device using compound PPTPB as ETL
Device structure as FIG. 2:
ITO/NPB (30 nm)/6 wt % FIrpic: CBP (30 nm)/PPTPB(30 nm)/LiF(0.5)/Al(100 nm)
CIE coordinate: X=0.15, Y=0.22
Turn-on voltage: 3.8V
Maximal brightness: 19800 cd/m$^2$ (12V)
Current efficiency: 11 cd/A Example 18

Synthesis of 4,4'-(6,6'-(1,2-phenylene)bis(2-phenyl-3-(trifluoromethyl)pyridine-6,4-diyl))-dibenzonitrile (PBTPD I)

2-bromo-3,3,3-trifluoro-1-phenylpropan-1-one and pyridine (1:1 in molar ratio) were stirred at 25° C. for 13 hours in dichloromathane (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, 1,2-diacetylbenzene and 4-cyanobenzaldehyde (3:1:3 in molar ratio) were added into a three-necked flask. And then tetrahydrofuran (20 times (weight) of the total amount of the resulted pyridinium bromide, 1,2-diacetylbenzene and 4-cyanobenzaldehyde) and catalysis amount ammonium acetate (10 molar % of the resulted pyridinium bromide) were added therein. The mixtures were refluxed for 24 hours, then crude product was obtained. Finally the multi-aryl substituted pyridine derivative was obtained via silicon gel chromatography column with CH$_2$Cl$_2$/Petroleum ether(3:1 v/v) as the eluent. The yield was about 55%.

m/z: 722.19 (100.0%), 723.19 (49.1%), 724.20 (11.2%), 725.20 (1.7%).

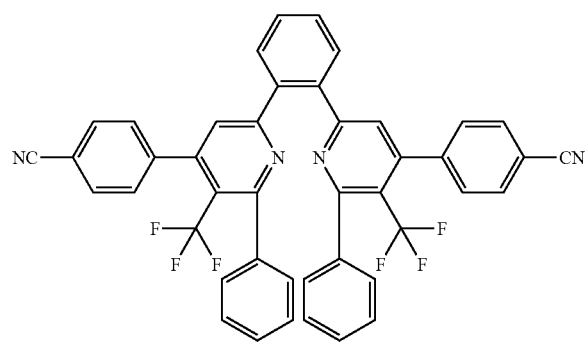

OLED device using compound PBTPD I as ETL

Device structure as FIG. 2:

ITO/NPB(75 nm)/ADN:TBP(30 nm)/PBTPD I (35 nm)/ LiF(0.5 nm)/MgAg(100 nm)

CIE coordinate: X=0.16, Y=0.22

Turn-on voltage: 3.8V

Maximal brightness: 20000 cd/m$^2$ (12V)

Current efficiency: 5.8 cd/A

Example 19

Synthesis of 6,6'-(1,2-phenylene)bis(2,4-diphenylnicotinonitrile) (PBDNT)

2-bromo-3-oxo-3-phenylpropanenitrile and pyridine (1:1 in molar ratio) were stirred at 25° C. for 15 hours in ethanol (20 times (weight) of the total amount of 2-bromo-3-oxo-3-phenylpropanenitrile and pyridine) then filtrated, and the resulted solids were washed with water, thereby pyridinium bromide was obtained.

The resulted pyridinium bromide, 1,2-diacetylbenzene and benzaldehyde (2:1:2 in molar ratio) were added into a three-necked flask. And then acetic acid (20 times (weight) of the total amount of the resulted pyridinium bromide, 1,2-diacetylbenzene and benzaldehyde) and catalysis amount ammonium acetate (10 molar % of the resulted pyridinium bromide) were added therein. The mixtures were refluxed for 26 hours, then crude product was obtained. Finally the multi-aryl substituted pyridine derivative was obtained via recrystallization with o-dichlorobenzene. The yield was about 65%.

m/z: 586.22 (100.0%), 587.22 (45.7%), 588.22 (10.7%), 589.23 (1.5%), 587.21 (1.5%).

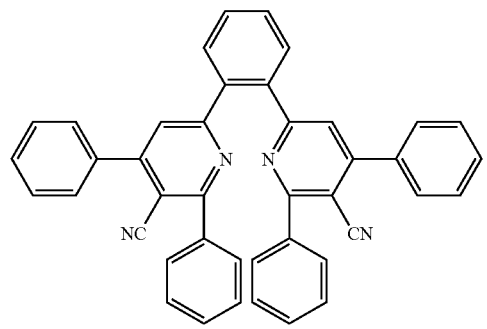

OLED device using compound PBDNT as HBL

Device structure as FIG. 1:

ITO/NPB(75 nm)/ADN:TBP(30 nm)/PBDNT(5 nm)/ Alq3(30 nm)/LiF(0.5 nm)/MgAg(100 nm)

CIE coordinate: X=0.16, Y=0.22

Turn-on voltage: 3.8V

Maximal brightness: 20000 cd/m$^2$ (12V)

Current efficiency: 5.8 cd/A

Example 20

Synthesis of 6,6'-(1,2-phenylene) bis(4-(4-cyanophenyl)-2-phenylnicotinonitrile) (PBCPN)

2-bromo-3-oxo-3-phenylpropanenitrile and pyridine (1:1 in molar ratio) were stirred at 25° C. for 10 hours in methanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, 1,2-diacetylbenzene and 4-formylbenzonitrile (2:1:2 in molar ratio) were added into a three-necked flask. And then dioxane (20 times (weight) of the total amount of the resulted pyridinium bromide, 1,2-diacetylbenzene and 4-formylbenzonitrile) and catalysis amount ammonium formate (10 molar % of the resulted pyridinium bromide) were added therein. The mixtures were refluxed for 25 hours, then crude product was obtained. Finally the multi-aryl substituted pyridine derivative was obtained via recrystallization with o-dichlorobenzene. The yield was about 55%.

m/z: 698.34 (100.0%), 699.34 (55.6%), 700.35 (14.6%), 701.35 (2.6%)

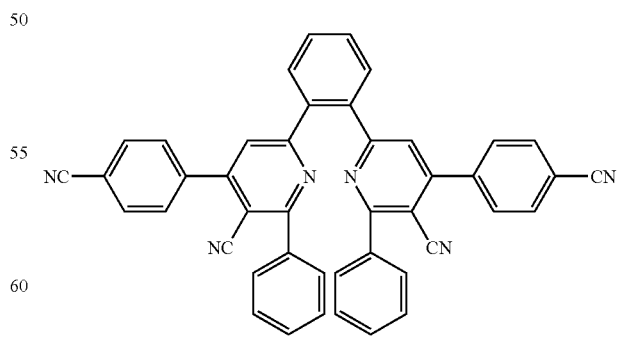

OLED device using compound PBCPN as ETL

Device structure as FIG. 2:

ITO/NPB(75 nm)/ADN:TBP(30 nm)/PBCPN (35 nm)/ LiF(0.5 nm)/MgAg(100 nm)

CIE coordinate: X=0.15, Y=0.22
Turn-on voltage: 4.5V
Maximal brightness: 20020 cd/m² (12V)
Current efficiency: 5.8 cd/A Example 21

Synthesis of diethyl 6,6'-(1,2-phenylene)bis(2,4-diphenylnicotinate) (PBNN I)

Ethyl 2-bromo-3-oxo-3-phenylpropanoate and pyridine (1:1 in molar ratio) were stirred at 25° C. for 12 hours in dichloromethane (20 times (weight) of the total amount of ethyl 2-bromo-3-oxo-3-phenylpropanoate and pyridine), then filtrated, and the resulted solids were washed with water, thereby pyridinium bromide was obtained.

The pyridinium bromide, 1,2-diacetylbenzene and benzaldehyde (2:1:2 in molar ratio) were added into a three-necked flask. And then tetrahydrofuran (20 times (weight) of the total amount of the resulted pyridinium bromide, 1,2-diacetylbenzene and benzaldehyde) and catalysis amount ammonium formate (10 molar % of the resulted pyridinium bromide) were added therein. The mixtures were refluxed for 27 hours, then crude product was obtained. Finally the multi-aryl substituted pyridine derivative was obtained via silicon gel chromatography column with CH₂Cl₂/Petroleum ether(3:1 v/v) as the eluent. The yield was about 60%.

m/z: 680.27 (100.0%), 681.27 (50.3%), 682.27 (13.3%), 683.28 (2.4%)

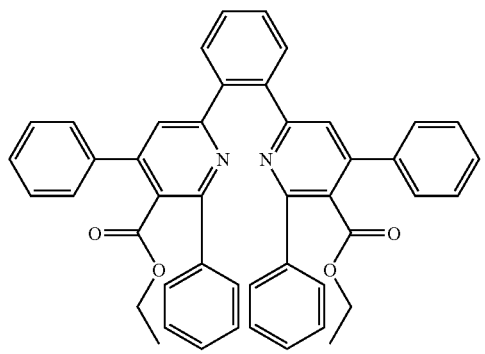

OLED device using compound PBNN I as ETL
Device structure as FIG. 2:
ITO/NPB(75 nm)/ADN(30 nm)/PBNN I (35 nm)/LiF(0.5 nm)/MgAg(100 nm)
CIE coordinate: X=0.15, Y=0.08
Turn-on voltage: 4.1V
Maximal brightness: 19800 cd/m² (12V)
Current efficiency: 4.7 cd/A Example 22

Synthesis of 6,6'-(1,2-phenylene)bis(2,4-diphenylpyridine-3,5-dicarbonitrile) (PTPPD I)

2-bromo-3-oxo-3-phenylpropanenitrile and pyridine (1:1 in molar ratio) were stirred at 25° C. for 13 hours in ethanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, 3,3'-(1,2-phenylene) bis (3-oxopropanenitrile) and benzaldehyde (2:1:2 in molar ratio) were added into a three-necked flask. And then dioxane (20 times (weight) of the total amount of the resulted pyridinium bromide, 3,3'-(1,2-phenylene) bis(3-oxopropanenitrile) and benzaldehyde) and catalysis amount ammonium acetate (10 molar % of the resulted pyridinium bromide) were added therein. The mixtures were refluxed for 23 hours, then crude product was obtained. Finally the multi-aryl substituted pyridine derivative was obtained via silicon gel chromatography column with CH₂Cl₂/Petroleum ether(3:1 v/v) as the eluent. The yield was about 45%.

m/z: 636.21 (100.0%), 637.21 (47.9%), 638.21 (12.1%), 637.20 (2.2%), 639.22 (1.7%)

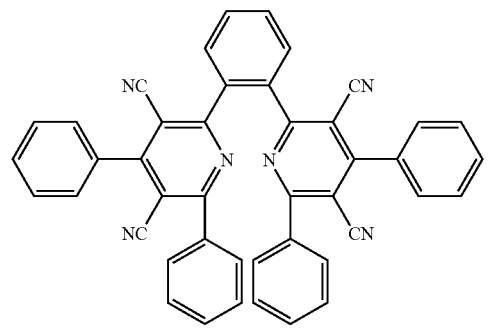

OLED device using compound PTPPD I as ETL
Device structure as FIG. 2:
ITO/NPB(75 nm)/ADN (30 nm)/PTPPD I (35 nm)/LiF(0.5 nm)/MgAg(100 nm)
CIE coordinate: X=0.15, Y=0.08
Turn-on voltage: 4.1V
Maximal brightness: 19800 cd/m² (12V)
Current efficiency: 4.7 cd/A Example 23

Synthesis of 6,6'-(1,2-phenylene) bis(4-(4-tert-butylphenyl)-2-phenylpyridine-3,5-dicarbonitrile) (PTPPD I)

2-bromo-3-oxo-3-phenylpropanenitrile and pyridine (1:1 in molar ratio) were stirred at 25° C. for 12 hours in methanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, 3,3'-(1,2-phenylene)bis (3-oxopropanenitrile) and 4-tert-butylbenzaldehyde (2:1:2 in molar ratio) were added into a three-necked flask. And then acetic acid (20 times (weight) of the total amount of the resulted pyridinium bromide, 3,3'-(1,2-phenylene)bis(3-oxopropanenitrile) and 4-tert-butylbenzaldehyde) and catalysis amount ammonium acetate (10 molar % of the resulted pyridinium bromide) were added therein. The mixtures were refluxed for 23 hours, then crude product was obtained. Finally the multi-aryl substituted pyridine derivative was obtained via recrystallization with o-dichlorobenzene. The yield was about 55%.

m/z: 748.33 (100.0%), 749.33 (58.5%), 750.34 (15.8%), 751.34 (3.2%), 750.33 (1.3%)

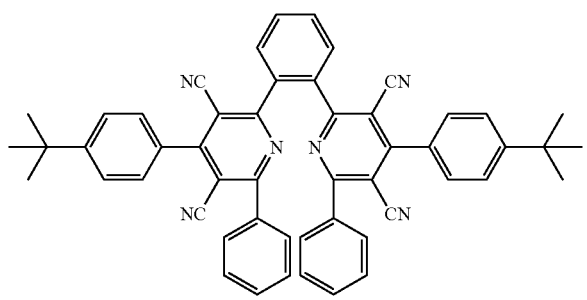

OLED device using compound PTPPD I as ETL
Device structure as FIG. 2:
ITO/NPB(70 nm)/5 tw % DSA-Ph:MADN(40 nm)/PT-PPD I (20 nm)/LiF(0.5)/Al(100 nm)
CIE coordinate: X=0.14, Y=0.20
Turn-on voltage: 4.0V
Maximal brightness: 20000 cd/m$^2$ (12V)
Current efficiency: 10 cd/A Example 24

Synthesis of 1,2-bis(4-(furan-3-yl)-6-phenyl-5-(trifluoromethyl)pyridin-2-yl)benzene (BFTPB I)

2-bromo-3,3,3-trifluoro-1-phenylpropan-1-one and pyridine (1:1 in molar ratio) were stirred at 25° C. for 11 hours in dicholomethane (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, 1,2-diacetylbenzene and furan-2-carbaldehyde (2:1:2 in molar ratio) were added into a three-necked flask. And then tetrahydrofuran (20 times (weight) of the total amount of the resulted pyridinium bromide, 1,2-diacetylbenzene and furan-2-carbaldehyde) and catalysis amount ammonium acetate (10 molar % of the resulted pyridinium bromide) were added therein. The mixtures were refluxed for 20 hours, then crude product was obtained. Finally the multi-aryl substituted pyridine derivative was obtained via recrystallization with o-dichlorobenzene. The yield was about 65%.

m/z: 652.16 (100.0%), 653.16 (42.2%), 654.17 (8.4%), 655.17 (1.3%)

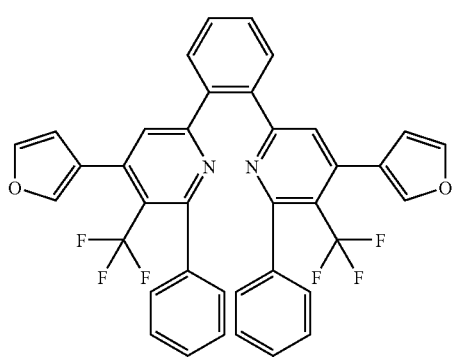

OLED device using compound BFTPB I as ETL
Device structure as FIG. 2:
ITO/NPB(30 nm)/6 wt % FIrpic:CBP (30 nm)/BFTPB I (30 nm)/LiF(0.5)/Al(100 nm)
CIE coordinate: X=0.15, Y=0.22
Turn-on voltage: 4.0V
Maximal brightness: 19800 cd/m$^2$ (12V)
Current efficiency: 10 cd/A Example 25

Synthesis of 1,4-bis(2-phenyl-6-p-tolyl-3-(trifluoromethyl)pyridin-4-yl)benzene (BPTTPB I)

2-bromo-3,3,3-trifluoro-1-phenylpropan-1-one and pyridine (1:1 in molar ratio) were stirred 25° C. for 10 hours in ethanol (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, terephthalaldehyde and p-methylacetophenone (2:1:2 in molar ratio) were added into a three-necked flask. And then acetic acid (20 times (weight) of the total amount of the resulted pyridinium bromide, terephthalaldehyde and p-methylacetophenone) and catalysis amount ammonium acetate (10 molar % of the resulted pyridinium bromide) were added therein. The mixtures were refluxed for 24 hours, then crude product was obtained. Finally the multi-aryl substituted pyridine derivative was obtained via silicon gel chromatography column with CH$_2$Cl$_2$/Petroleum ether(3:1 v/v) as the eluent. The yield was about 50%.

m/z: 700.23 (100.0%), 701.23 (48.3%), 702.24 (11.2%), 703.24 (1.8%)

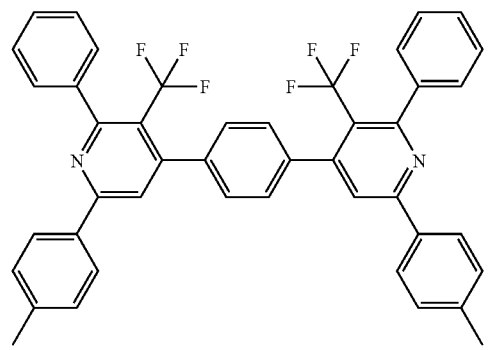

OLED device using compound BPTTPB II as ETL
Device structure as FIG. 2:
ITO/NPB(75 nm)/ADN:TBP(30 nm)/BPTTPB II (35 nm)/LiF(0.5 nm)/MgAg(100 nm)
CIE coordinate: X=0.14, Y=0.22
Turn-on voltage: 3.8V
Maximal brightness: 20000 cd/m$^2$ (12V)
Current efficiency: 5.8 cd/A Example 26

Synthesis of 1,4-bis(6-(biphenyl-4-yl)-2-phenyl-3-(trifluoromethyl)-pyridin-4-yl)benzene (BBPTPB)

2-bromo-3,3,3-trifluoro-1-phenylpropan-1-one and pyridine (1:1 in molar ratio) were stirred at 25° C. for 10 hours in methanol (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, terephthalaldehyde and 4-acetylbiphenyl (2:1:2 in molar ratio) were added into a three-necked flask. And then dioxane (20 times (weight) of the total amount of the resulted pyridinium bromide, terephthalaldehyde and 4-acetylbiphenyl) and catalysis amount ammonium formate (10 molar % of the resulted pyridinium bromide) were added therein. The mixtures were refluxed for 22 hours, then crude product was obtained. Finally the multi-aryl substituted pyridine derivative was obtained via silicon gel chromatography column with CH$_2$Cl$_2$/Petroleum ether(3:1) as the eluent. The yield was about 55%.

m/z: 824.26 (100.0%), 825.27 (58.8%), 826.27 (17.0%), 827.27 (3.3%)

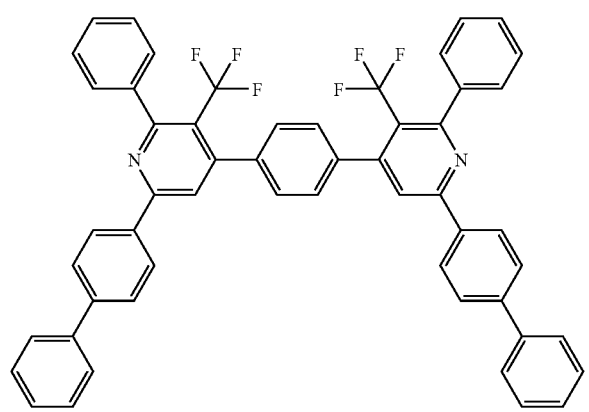

OLED device using compound BBPTPB as HBL
Device structure as FIG. 1:
ITO/NPB(75 nm)/ADN:TBP(30 nm)/BBPTPB(35 nm)/BPhen(30 nm)/LiF(0.5 nm)/MgAg(100 nm)
CIE coordinate: X=0.14, Y=0.22
Turn-on voltage: 3.8V
Maximal brightness: 20000 cd/m$^2$ (12V)
Current efficiency: 5.8 cd/A Example 27

Synthesis of 4,4'-(1,4-phenylene)bis(2-phenyl-6-p-tolylnicotinonitrile) (PBPTNN II)

2-bromo-3-oxo-3-phenylpropanenitrile and pyridine (1:1 in molar ratio) were stirred at 25° C. for 11 hours in dichloromethane (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, p-methylacetophenone and terephthalaldehyde (2:2:1-3:3:1 in molar ratio) were added into a three-necked flask. And then tetrahydrofuran (20 times (weight) of the total amount of the resulted pyridinium bromide, p-methylacetophenone and terephthalaldehyde) and catalysis amount ammonium formate (10 molar % of the resulted pyridinium bromide) were added therein. The mixtures were refluxed for 28 hours, then crude product was obtained. Finally the multi-aryl substituted pyridine derivative was obtained via recrystallization with o-dichlorobenzene. The yield was about 60%.

m/z: 614.25 (100.0%), 615.25 (47.9%), 616.25 (11.8%), 617.26 (1.7%), 615.24 (1.5%)

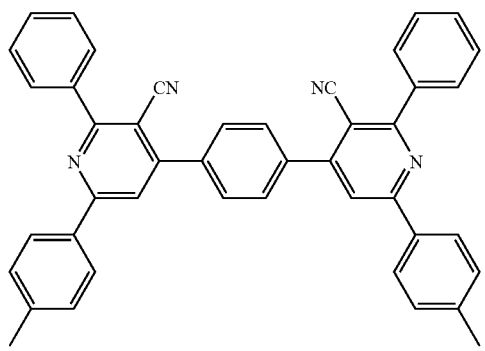

OLED device using compound PBPTNN II as ETL
Device structure as FIG. 2:
ITO/NPB(75 nm)/ADN:TBP(30 nm)/PBPTNN II (35 nm)/LiF(0.5 nm)/MgAg(100 nm)
CIE coordinate: X=0.15, Y=0.22
Turn-on voltage: 4.0V
Maximal brightness: 19500 cd/m$^2$ (12V)
Current efficiency: 5.2 cd/A Example 28

Synthesis of 4,4'-(1,4-phenylene) bis(6-(4-tert-butylphenyl)-2-phenylnicotinonitrile) (PBPNN)

2-bromo-3-oxo-3-phenylpropanenitrile and pyridine (1:1 in molar ratio) were stirred at 25° C. for 12 hours in ethanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, p-tert-butylacetophenone and terephthalaldehyde (2:2:1 in molar ratio) were added into a three-necked flask. And then dioxane (20 times (weight) of the total amount of the resulted pyridinium bromide, p-tert-butylacetophenone and terephthalaldehyde) and catalysis amount ammonium formate (10 molar % of the resulted pyridinium bromide) were added therein. The mixtures were refluxed for 24 hours, then crude product was obtained. Finally the multi-aryl substituted pyridine derivative was obtained via recrystallization with o-dichlorobenzene. The yield was about 50%.

m/z: 698.34 (100.0%), 699.34 (55.6%), 700.35 (14.6%), 701.35 (2.6%).

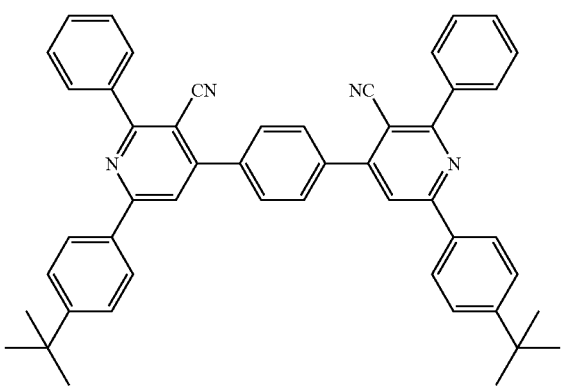

OLED device using compound PBPNN as HBL
Device structure as FIG. 1:
ITO/NPB(75 nm)/ADN:TBP(30 nm)/PBPNN(35 nm)/Alq3(30 nm)/LiF(0.5 n m)/MgAg(100 nm)
CIE coordinate: X=0.15, Y=0.22
Turn-on voltage: 4.0V
Maximal brightness: 19500 cd/m² (12V)
Current efficiency: 5.2 cd/A Example 29

Synthesis of diethyl 4,4'-(1,4-phenylene) bis(6-(biphenyl-4-yl)-2-phenylnicotinate) (PBBPN)

Ethyl 2-bromo-3-oxo-3-phenylpropanoate and pyridine (1:1 in molar ratio) were stirred at 25° C. for 13 hours in methanol (20 times (weight) of the total amount of Ethyl 2-bromo-3-oxo-3-phenylpropanoate and pyridine), then filtrated, and the resulted solids were washed with water, thereby pyridinium bromide was obtained.

The resulted pyridinium bromide, terephthalaldehyde and 4-acetylbiphenyl (2:1:2 in molar ratio) were added into a three-necked flask. And then acetic acid (20 times (weight) of the total amount of the resulted pyridinium bromide, terephthalaldehyde and 4-acetylbiphenyl) and catalysis amount ammonium acetate (10 molar % of the resulted pyridinium bromide) were added therein. The mixtures were refluxed for 25 hours, then crude product was obtained. Finally the multi-aryl substituted pyridine derivative was obtained via silicon gel chromatography column with CH₂Cl₂/Petroleum ether(3:1) as the eluent. The yield was about 55%.
m/z: 832.33 (100.0%), 833.33 (63.6%), 834.34 (19.8%), 835.34 (4.6%), 834.33 (1.3%)

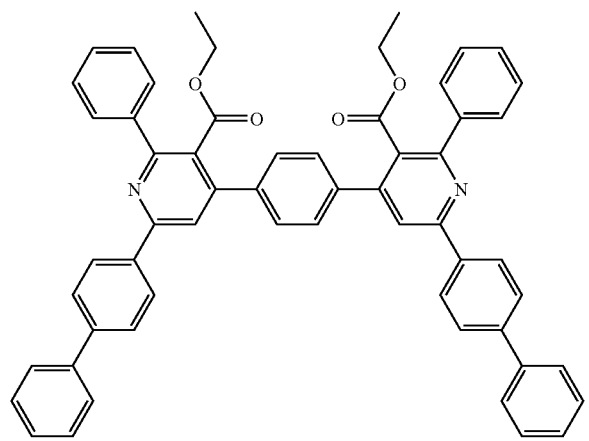

OLED device using compound PBBPN as ETL
Device structure as FIG. 2:
ITO/NPB(75 nm)/ADN(30 nm)/PBBPN (35 nm)/LiF(0.5 nm)/MgAg(100 nm)
CIE coordinate: X=0.15, Y=0.09
Turn-on voltage: 4.0V
Maximal brightness: 19800 cd/m² (12V)
Current efficiency: 4.8 cd/A Example 30

Synthesis of 4,4'-(1,4-phenylene)bis(2-phenyl-6-p-tolylpyridine-3,5-dicarbonitrile) (PBPTDN)

2-bromo-3-oxo-3-phenylpropanenitrile and pyridine (1:1 in molar ratio) were stirred at 25° C. for 11 hours in dichloromethane (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, 3-oxo-3-p-tolylpropanenitrile and terephthalaldehyde (2:2:1 in molar ratio) were added into a three-necked flask. And then tertrahydrofuran (20 times (weight) of the total amount of the resulted pyridinium bromide, 3-oxo-3-p-tolylpropanenitrile and terephthalaldehyde) and catalysis amount ammonium acetate (10 molar % of the resulted pyridinium bromide) were added therein. The mixtures were refluxed for 23 hours, then crude product was obtained. Finally the multi-aryl substituted pyridine derivative was obtained via silicon gel chromatography column with CH₂Cl₂/Petroleum ether(3:1 v/v) as the eluent. The yield was about 45%.
m/z: 664.24 (100.0%), 665.24 (50.1%), 666.24 (13.2%), 665.23 (2.2%), 667.25 (2.0%)

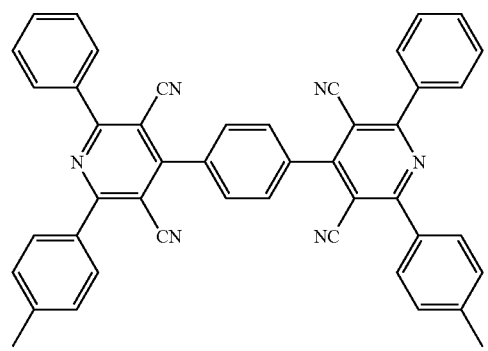

OLED device using compound PBPTDN as ETL
Device structure as FIG. 2:
ITO/NPB(70 nm)/5 tw % DSA-Ph:MADN(40)/PBPTDN (20 nm)/LiF(0.5)/Al(100 nm)
CIE coordinate: X=0.14, Y=0.21
Turn-on voltage: 3.8V
Maximal brightness: 20200 cd/m² (12V)
Current efficiency: 11 cd/A Example 31

Synthesis of 4,4'-(1,4-phenylene)bis(2-(4-tert-butylphenyl)-6-phenylpyridine-3,5-dicarbonitrile (PBBPD II)

2-bromo-3-oxo-3-phenylpropanenitrile and pyridine (1:1 in molar ratio) were stirred at 25° C. for 10 hours in ethanol (20 times (weight) of the total amount of 2-bromo-3-oxo-3-phenylpropanenitrile and pyridin e), then filtrated, the resulted solids were washed with water, thereby pyridinium bromide was obtained.

The resulted pyridinium bromide, 3-(4-tert-butylphenyl)-3-oxopropanenitrile and terephthalaldehyde (2:1:2 in molar ratio) were added into a three-necked flask. And then acetic acid (20 times (weight) of the total amount of the resulted pyridinium bromide, 3-(4-tert-butylphenyl)-3-oxopropanenitrile and terephthalaldehyde) and catalysis amount ammonium acetate (10 molar % of the resulted pyridinium bromide) were added therein. The mixtures were refluxed for 29 hours, then crude product was obtained. Finally the multi-aryl substituted pyridine derivative was obtained via recrystallization with o-dichlorobenzene. The yield was about 50%.

m/z: 748.33 (100.0%), 749.33 (58.5%), 750.34 (15.8%), 751.34 (3.2%), 750.33 (1.3%)

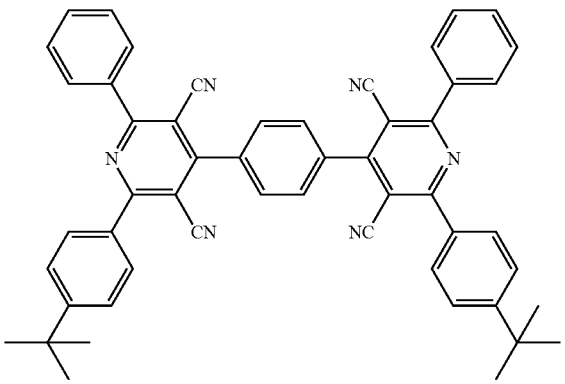

OLED device using compound PBBPD II as ETL
Device structure as FIG. 2:
ITO/NPB(75 nm)/ADN:TBP(30 nm)/PBBPD II (35 nm)/LiF(0.5 nm)/MgAg(100 nm)
CIE coordinate: X=0.15, Y=0.22
Turn-on voltage: 4.0V
Maximal brightness: 22000 cd/m$^2$ (12V)
Current efficiency: 5.4 cd/A Example 32

Synthesis of 1,4-bis(6-(furan-2-yl)-2-phenyl-3-(trifluoromethyl)pyridin-4-yl)benzene (BFPPB)

2-bromo-3,3,3-trifluoro-1-phenylpropan-1-one and pyridine (1:1 in molar ratio) were stirred at 25° C. for 13 hours in methanol (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, terephthalaldehyde and 1-(furan-2-yl)ethanone (2:1:2 in molar ratio) were added into a three-necked flask. And then dioxane (20 times (weight) of the total amount of the resulted pyridinium bromide, terephthalaldehyde and 1-(furan-2-yl)ethanone) and catalysis amount ammonium acetate (10 molar % of the resulted pyridinium bromide) were added therein. The mixtures were refluxed for 30 hours, then crude product was obtained. Finally the multi-aryl substituted pyridine derivative was obtained via silicon gel chromatography column with CH$_2$Cl$_2$/Petroleum Petroleum ether(3:1 v/v) as the eluent. The yield was about 65%.
m/z: 652.16 (100.0%), 653.16 (42.2%), 654.17 (8.4%), 655.17 (1.3%)

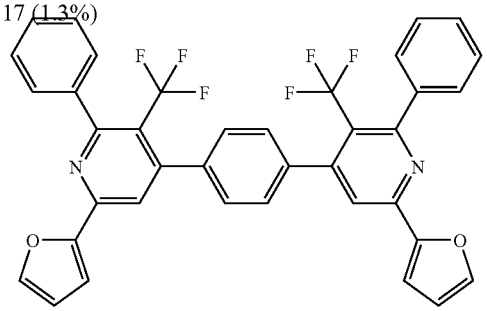

OLED device using compound BFPPB as ETL
Device structure as FIG. 2:
ITO/NPB(30 nm)/6 wt % FIrpic:CBP(30 nm)/BFPPB(30 nm)/LiF(0.5)/Al(100 nm)

CIE coordinate: X=0.15, Y=0.23
Turn-on voltage: 4.2V
Maximal brightness: 19900 cd/m$^2$ (12V)
Current efficiency: 10.5 cd/A Example 33

Synthesis of 1,3-bis(2-phenyl-6-p-tolyl-3-(trifluoromethyl)pyridin-4-yl)benzene (BPTFPB)

2-bromo-3,3,3-trifluoro-1-phenylpropan-1-one and pyridine (1:1 in molar ratio) were stirred at 25° C. for 14 hours in dichloromethane (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, m-phthalaldehyde and p-methylacetophenone (2:1:2 in molar ratio) were added into a three-necked flask. And then tetrahydrofuran (20 times (weight) of the total amount of the resulted pyridinium bromide, m-phthalaldehyde and p-methylacetophenone) and catalysis amount ammonium formate (10 molar % of the resulted pyridinium bromide) were added therein. The mixtures were refluxed for 30 hours, then crude product was obtained. Finally the multi-aryl substituted pyridine derivative was obtained via recrystallization with o-dichlorobenzene. The yield was about 55%.
m/z: 700.23 (100.0%), 701.23 (48.3%), 702.24 (11.2%), 703.24 (1.8%)

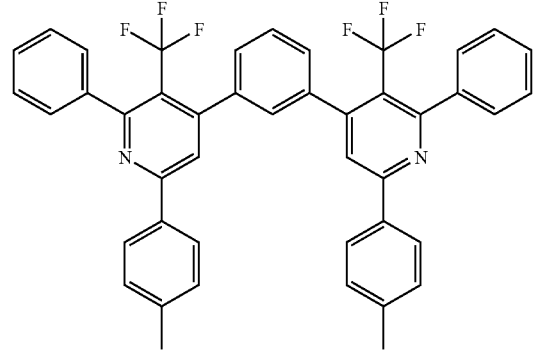

OLED device using compound BPTFPB as ETL
Device structure as FIG. 2:
ITO/NPB(75 nm)/ADN:TBP(30 nm)/BPTFPB (35 nm)/LiF(0.5 nm)/MgAg(100 nm)
CIE coordinate: X=0.15, Y=0.22
Turn-on voltage: 3.9V
Maximal brightness: 19000 cd/m$^2$ (12V)
Current efficiency: 4.0 cd/A Example 34

Synthesis of 1,3-bis(6-(4-methoxyphenyl)-2-phenyl-3-(trifluoromethyl)-pyridin-4-yl)benzene (BMPTPB II)

2-bromo-3,3,3-trifluoro-1-phenylpropan-1-one and pyridine (1:1 in molar ratio) were stirred at 25° C. for 13 hours in ethanol (20 times (weight) of the total amount of 2-bromo-3, 3,3-trifluoro-1-phenylpropan-1-one and pyridin e), then filtrated, and the resulted solids were washed with water, thereby pyridinium bromide was obtained.

The resulted pyridinium bromide, m-phthalaldehyde and p-methoxyacetophenone (2:1:2 in molar ratio) were added into a three-necked flask. And then dioxane (20 times (weight) of the total amount of the resulted pyridinium bromide, m-phthalaldehyde and p-methoxyacetophenone) and catalysis amount ammonium acetate (10 molar % of the resulted pyridinium bromide) were added therein. The mixtures were refluxed for 22 hours, then crude product was obtained. Finally the multi-aryl substituted pyridine derivative was obtained via recrystallization with o-dichlorobenzene. The yield was about 55%.

m/z: 732.22 (100.0%), 733.22 (48.3%), 734.23 (11.7%), 735.23 (1.9%)

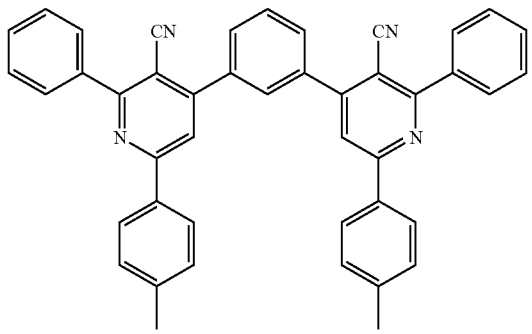

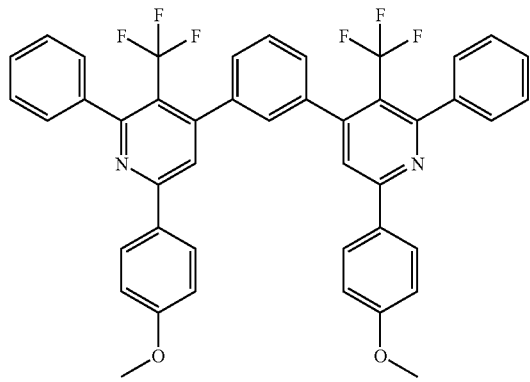

OLED device using compound BMPTPB II as ETL
Device structure as FIG. 2:
ITO/NPB(75 nm)/ADN:TBP(30 nm)/BMPTPB II (35 nm)/LiF(0.5 nm)/MgAg(100 nm)
CIE coordinate: X=0.14, Y=0.20
Turn-on voltage: 3.98V
Maximal brightness: 20100 cd/m² (12V)
Current efficiency: 5.8 cd/A Example 35

Synthesis of 4,4'-(1,3-phenylene)bis(2-phenyl-6-p-tolylnicotinonitrile) (PBPTCN)

2-bromo-3-oxo-3-phenylpropanenitrile and pyridine (1:1 in molar ratio) were stirred at 25° C. for 10 hours in methanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, p-methylacetophenone and m-phthalaldehyde (2:1:2 in molar ratio) were added into a three-necked flask. And then acetic acid (20 times (weight) of the total amount of the resulted pyridinium bromide, p-methylacetophenone and m-phthalaldehyde) and catalysis amount ammonium acetate (10 molar % of the resulted pyridinium bromide) were added therein. The mixtures were refluxed for 23 hours, then crude product was obtained. Finally the multi-aryl substituted pyridine derivative was obtained via silicon gel chromatography column with CH₂Cl₂/Petroleum Petroleum ether(3:1 v/v) as the eluent. The yield was about 45%.

m/z: 614.25 (100.0%), 615.25 (47.9%), 616.25 (11.8%), 617.26 (1.7%), 615.24 (1.5%)

OLED device using compound PBPTCN HBL
Device structure as FIG. 1:
ITO/NPB(75 nm)/ADN:TBP(30 nm)/PBPTCN(35 nm)/BPhen(30 nm)/LiF(0. nm)/MgAg(100 nm)
CIE coordinate: X=0.14, Y=0.20
Turn-on voltage: 3.98V
Maximal brightness: 20100 cd/m² (12V)
Current efficiency: 5.8 cd/A Example 36

Synthesis of 4,4'-(1,3-phenylene) bis(6-(4-tert-butylphenyl)-2-phenylnicotinonitrile) (PBTPNN II)

2-bromo-3-oxo-3-phenylpropanenitrile and pyridine (1:1 in molar ratio) were stirred at 25° C. for 11 hours in dichloromethane (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, p-tert-butylacetophenone and m-phthalaldehyde (2:2:1 in molar ratio) were added into a three-necked flask. And then tetrahydrofuran (20 times (weight) of the total amount of the resulted pyridinium bromide, p-tert-butylacetophenone and m-phthalaldehyde) and catalysis amount ammonium formate (10 molar % of the resulted pyridinium bromide) were added therein. The mixtures were refluxed for 21 hours, then crude product was obtained. Finally the multi-aryl substituted pyridine derivative was obtained via silicon gel chromatography column with CH₂Cl₂/Petroleum Petroleum ether(3:1 v/v) as the eluent. The yield was about 55%.

m/z: 698.34 (100.0%), 699.34 (55.6%), 700.35 (14.6%), 701.35 (2.6%)

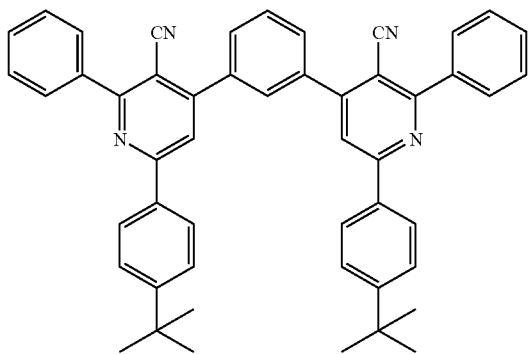

OLED device using compound PBTPNN II as HBL
Device structure as FIG. 1:
ITO/NPB(75 nm)/ADN:TBP(30 nm)/PBTPNN II (35 nm)/Alq3(30 nm)/LiF(0.5 nm)/MgAg(100 nm)
CIE coordinate: X=0.14, Y=0.20
Turn-on voltage: 3.98V
Maximal brightness: 20100 cd/m$^2$ (12V)
Current efficiency: 5.8 cd/A Example 37

Synthesis of Diethyl 4,4'-(1,3-phenylene)bis(6-(4-methoxyphenyl)-2-phenyl-nicotinate) (PBMPNN II)

Ethyl 2-bromo-3-oxo-3-phenylpropanoate and pyridine (1:1 in molar ratio) were stirred at 25° C. for 12 hours in ethanol (20 times (weight) of the total amount of ethyl 2-bromo-3-oxo-3-phenylpropanoate and pyridine), then filtrated, and the resulted solids were washed with water, thereby pyridinium bromide was obtained.

The resulted pyridinium bromide, m-phthalaldehyde and p-methoxyacetophenone (3:1:1 in molar ratio) were added into a three-necked flask. And then acetic acid (20 times (weight) of the total amount of the resulted pyridinium bromide, m-phthalaldehyde and p-methoxyacetophenone) and catalysis amount ammonium acetate (10 molar % of the resulted pyridinium bromide) were added therein. The mixtures were refluxed for 20 hours, then crude product was obtained. Finally the multi-aryl substituted pyridine derivative was obtained via recrystallization with o-dichlorobenzene. The yield was about 60%.

m/z: 740.29 (100.0%), 741.29 (53.3%), 742.30 (13.6%), 743.30 (2.9%), 742.29 (1.6%)

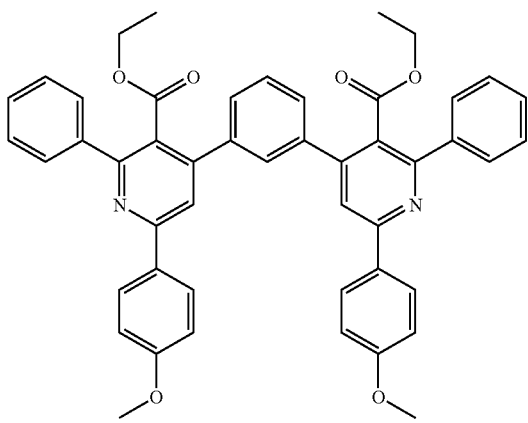

OLED device using compound PBMPNN II as ETL
Device structure as FIG. 2:
ITO/NPB(75 nm)/ADN(30 nm)/PBMPNN II (35 nm)/LiF (0.5 nm)/MgAg(100 nm)
CIE coordinate: X=0.14, Y=0.09
Turn-on voltage: 4.1V
Maximal brightness: 19850 cd/m$^2$ (12V)
Current efficiency: 4.8 cd/A Example 38

Synthesis of 4,4'-(1,3-phenylene)bis(2,6-diphenyl-5-(trifluoromethyl)nicotinonitrile) (PBDFNN)

2-bromo-3-oxo-3-phenylpropanenitrile and pyridine (1:1 in molar ratio) were stirred at 25° C. for 10 hours in methanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, m-phthalaldehyde and 3,3,3-trifluoro-1-phenylpropan-1-one (2:1:2 in molar ratio) were added into a three-necked flask. And then acetic acid (20 times (weight) of the total amount of the resulted pyridinium bromide, m-phthalaldehyde and 3,3,3-trifluoro-1-phenylpropan-1-one) and catalysis amount ammonium acetate (10 molar % of the resulted pyridinium bromide) were added therein. The mixtures were refluxed for 26 hours, then crude product was obtained. Finally the multi-aryl substituted pyridine derivative was obtained via recrystallization with o-dichlorobenzene. The yield was about 60%.

m/z: 722.19 (100.0%), 723.19 (49.1%), 724.20 (11.2%), 725.20 (1.7%)

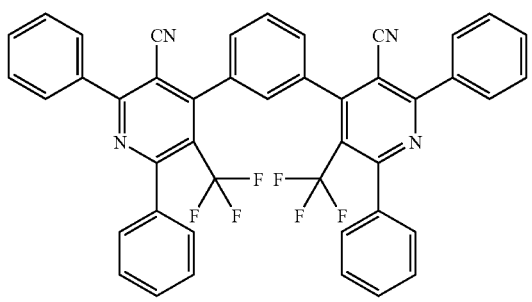

OLED device using compound PBDFNN as ETL
Device structure as FIG. 2:
ITO/NPB(70 nm)/5 tw % DSA-Ph:MADN(40)/PBDFNN (20 nm)/LiF(0.5)/Al(100 nm)
CIE coordinate: X=0.14, Y=0.20
Turn-on voltage: 3.9V
Maximal brightness: 20200 cd/m$^2$ (12V)
Current efficiency: 10 cd/A Example 39

Synthesis of 4,4'-(1,3-phenylene) bis(2-(4-tert-butylphenyl)-6-phenylpyridine-3,5-dicarbonitrile) (PBTPD II)

2-bromo-3-oxo-3-phenylpropanenitrile and pyridine (1:1 in molar ratio) were stirred at 25° C. for 10 hours in dichloromethane (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, 3-(4-tert-butylphenyl)-3-oxopropanenitrile and m-phthalaldehyde (2:2:1 in molar ratio) were added into a three-necked flask. And then tetrahydrofuran (20 times (weight) of the total amount of the resulted pyridinium bromide, 3-(4-tert-butylphenyl)-3-oxopropanenitrile and m-phthalaldehyde) and catalysis amount ammonium acetate (10 molar % of the resulted pyridinium bromide) were added therein. The mixtures were refluxed for 25 hours, then crude product was obtained. Finally the multi-aryl substituted pyridine derivative was obtained via silicon gel chromatography column with CH$_2$Cl$_2$/Petroleum ether (3:1 v/v) as the eluent. The yield was about 50%.

m/z: 748.33 (100.0%), 749.33 (58.5%), 750.34 (15.8%), 751.34 (3.2%), 750.33 (1.3%)

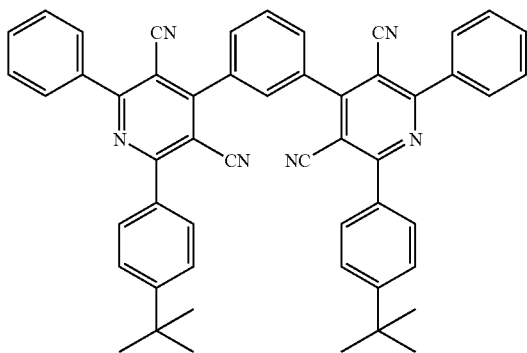

OLED device using compound PBTPD II as ETL
Device structure as FIG. 2:
ITO/NPB(70 nm)/5 tw % DSA-Ph:MADN(40 nm)/PBTPD II (20 nm)/LiF(0.5)/Al(100 nm)
CIE coordinate: X=0.14, Y=0.20
Turn-on voltage: 3.9V
Maximal brightness: 20200 cd/m$^2$ (12V)
Current efficiency: 10 cd/A Example 40

Synthesis of 1,3-bis(6-(furan-2-yl)-2-phenyl-3-(trifluoromethyl)pyridin-4-yl)benzene (BFPTPB II)

2-bromo-3,3,3-trifluoro-1-phenylpropan-1-one and pyridine (1:1 in molar ratio) were stirred at 25° C. for 13 hours in ethanol (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, m-phthalaldehyde and 1-(furan-2-yl)ethanone (2:1:2 in molar ratio) were added into a three-necked flask. And then dioxane (20 times (weight) of the total amount of the resulted pyridinium bromide, m-phthalaldehyde and 1-(furan-2-yl)ethanone) and catalysis amount ammonium formate (10 molar % of the resulted pyridinium bromide) were added therein. The mixtures were refluxed for 20 hours, then crude product was obtained. Finally the multi-aryl substituted pyridine derivative was obtained via silicon gel chromatography column with CH$_2$Cl$_2$/Petroleum Petroleum ether(3:1 v/v) as the eluent. The yield was about 55%.
m/z: 652.16 (100.0%), 653.16 (42.2%), 654.17 (8.4%), 655.17 (1.3%)

OLED device using compound BFPTPB II as ETL
Device structure as FIG. 2:
ITO/NPB (30 nm)/6 wt % FIrpic:CBP(30 nm)/BFPTPB II (30 nm)/LiF(0.5)/Al(100 nm)
CIE coordinate: X=0.15, Y=0.20
Turn-on voltage: 4.0V
Maximal brightness: 19900 cd/m$^2$ (12V)
Current efficiency: 11 cd/A Example 41

Synthesis of 1,2-bis(6-(4-methoxyphenyl)-2-phenyl-3-(trifluoromethyl)pyridin-4-yl)benzene (BPTPB II)

2-bromo-3,3,3-trifluoro-1-phenylpropan-1-one and pyridine (1:1 in molar ratio) were stirred 25° C. for 14 hours in methanol (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, o-phthalaldehyde and p-methoxyacetophenone (2:1:2 in molar ratio) were added into a three-necked flask. And then acetic acid (20 times (weight) of the total amount of the resulted pyridinium bromide, o-phthalaldehyde and p-methoxyacetophenone) and a little ammonium acetate (10 molar % of the resulted pyridinium bromide) were added therein. The mixtures were refluxed for 27 hours, then crude product was obtained. Finally the multi-aryl substituted pyridine derivative was obtained via recrystallization with o-dichlorobenzene. The yield was about 45%.
m/z: 732.22 (100.0%), 733.22 (48.3%), 734.23 (11.7%), 735.23 (1.9%)

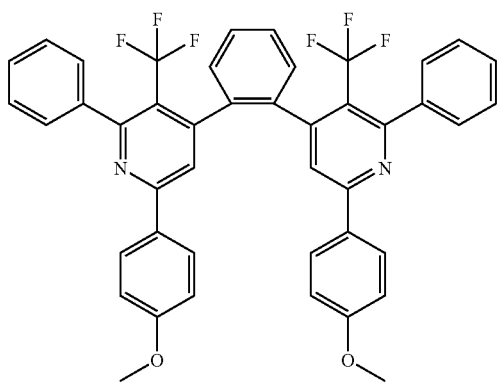

OLED device using compound BPTPB II as ETL
Device structure as FIG. 2:
ITO/NPB (30 nm)/6 wt % FIrpic:CBP (30 nm)/BPTPB II (30 nm)/LiF(0.5)/Al(100 nm)
CIE coordinate: X=0.15, Y=0.20
Turn-on voltage: 4.0V
Maximal brightness: 19900 cd/m$^2$ (12V)
Current efficiency: 11 cd/A Example 42

Synthesis of 1,2-bis(6-(biphenyl-4-yl)-2-phenyl-3-(trifluoromethyl)-pyridin-4-yl)benzene (BPPTPB)

2-bromo-3,3,3-trifluoro-1-phenylpropan-1-one and pyridine (1:1 in molar ratio) were stirred at 25° C. for 15 hours in dichloromethane (20 times (weight) of the total amount of 2-bromo-3,3,3-trifluoro-1-phenylpropan-1-one and pyridine), then filtrated, and the resulted solids were washed with water, thereby pyridinium bromide was obtained.

The resulted pyridinium bromide, o-phthalaldehyde and 1-(biphenyl-4-yl)ethanone (2:1:2 in molar ratio) were added into a three-necked flask. And then tetrahydrofuran (20 times (weight) of the total amount of the resulted pyridinium bromide, o-phthalaldehyde and 1-(biphenyl-4-yl)ethanone) and catalysis amount ammonium acetate (10 molar % of the resulted pyridinium bromide) were added therein. The mixtures were refluxed for 28 hours, then crude product was obtained. Finally the multi-aryl substituted pyridine derivative was obtained via silicon recrystallization with o-dichlorobenzene. The yield was about 55%.

m/z: 824.26 (100.0%), 825.27 (58.8%), 826.27 (17.0%), 827.27 (3.3%).

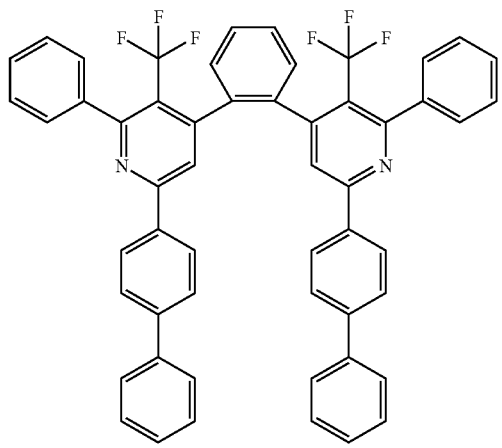

OLED device using compound BPPTPB as ETL
Device structure as FIG. 2:
ITO/NPB(75 nm)/ADN:TBP(30 nm)/BPPTPB (35 nm)/LiF(0.5 nm)/MgAg(100 nm)
CIE coordinate: X=0.14, Y=0.20
Turn-on voltage: 3.8V
Maximal brightness: 20100 cd/m$^2$ (12V)
Current efficiency: 5.8 cd/A Example 43

Synthesis of 4,4'-(1,2-phenylene)bis(6-(biphenyl-4-yl)-2-phenylnicotinonitrile) (PBCPNN)

2-bromo-3-oxo-3-phenylpropanenitrile and pyridine (1:1 in molar ratio) were stirred at 25° C. for 15 hours in ethanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, o-phthalaldehyde and 1-(biphenyl-4-yl)ethanone (2:1:2 in molar ratio) were added into a three-necked flask. And then acetic acid (20 times (weight) of the total amount of the resulted pyridinium bromide, o-phthalaldehyde and 1-(biphenyl-4-yl)ethanone) and catalysis amount ammonium acetate (10 molar % of the resulted pyridinium bromide) were added therein. The mixtures were refluxed for 27 hours, then crude product was obtained. Finally the multi-aryl substituted pyridine derivative was obtained via silicon gel chromatography column with CH$_2$Cl$_2$/Petroleum Petroleum ether(3:1 v/v) as the eluent. The yield was about 65%.

m/z: 738.28 (100.0%), 739.28 (60.3%), 740.29 (17.0%), 741.29 (3.2%)

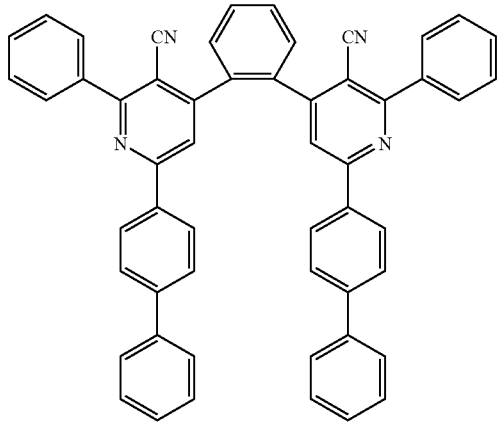

OLED device using compound PBCPNN as HBL
Device structure as FIG. 1:
ITO/NPB(75 nm)/ADN:TBP(30 nm)/PBCPNN(35 nm)/BPhen(30 nm)/LiF(0. nm)/MgAg(100 nm)
CIE coordinate: X=0.14, Y=0.20
Turn-on voltage: 3.8V
Maximal brightness: 20100 cd/m$^2$ (12V)
Current efficiency: 5.8 cd/A Example 44

Synthesis of 4,4'-(1,2-phenylene) bis(6-(4-tert-butylphenyl)-2-phenylnicotinonitrile) (PBTNN II)

2-bromo-3-oxo-3-phenylpropanenitrile and pyridine (1:1 in molar ratio) were stirred at 25° C. for 10 hours in methanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, o-phthalaldehyde and p-tert-butylacetophenone (2:1:2 in molar ratio) were added into a three-necked flask. And then dioxane (20 times (weight) of the total amount of the resulted pyridinium bromide, o-phthalaldehyde and p-tert-butylacetophenone) and catalysis amount ammonium acetate (10 molar % of the resulted pyridinium bromide) were added therein. The mixtures were refluxed for 22 hours, then crude product was obtained. Finally the multi-aryl substituted pyridine derivative was obtained via silicon gel chromatography column with CH$_2$Cl$_2$/Petroleum Petroleum ether(3:1 v/v) as the eluent. The yield was about 55%.

m/z: 698.34 (100.0%), 699.34 (55.6%), 700.35 (14.6%), 701.35 (2.6%)

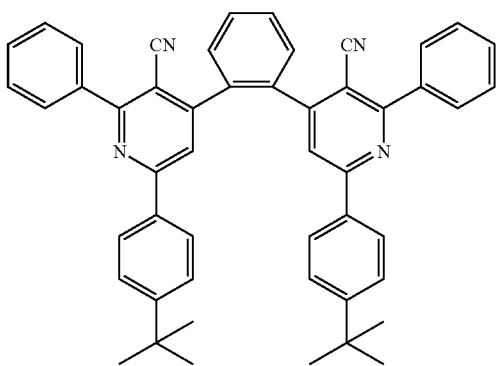

OLED device using compound PBTNN II as HBL

Device structure as FIG. 1:

ITO/NPB(75 nm)/ADN:TBP(30 nm)/PBTNN II (35 nm)/Alq3(30 nm)/LiF(0.5 nm)/MgAg(100 nm)

CIE coordinate: X=0.14, Y=0.20

Turn-on voltage: 3.8V

Maximal brightness: 20100 cd/m$^2$ (12V)

Current efficiency: 5.8 cd/A

Comparative Example 1

Preparing the OLED according to the methods of Example 44, except that the HBL 7 does not comprise the material provided by the present invention, i.e Device structure as FIG. 2:

OLED device using compound Alq3 as ETL

ITO/NPB(75 nm)/ADN:TBP(30 nm)/Alq3(30 nm)/LiF(0.5 nm)/MgAg(100 nm)

CIE coordinate: X=0.22, Y=0.25

Turn-on voltage: 5.4V

Maximal brightness: 14000 cd/m$^2$ (12V)

Current efficiency: 2.0 cd/A

Example 45

Synthesis of Diethyl 4,4'-(1,2-phenylene)bis(6-(4-methoxyphenyl)-2-phenyl-nicotinate) (PBNN II)

Ethyl 2-bromo-3-oxo-3-phenylpropanoate and pyridine (1:1 in molar ratio) were stirred at room for 12 hours in dichloromethane (20 times (weight) of the total amount of ethyl 2-bromo-3-oxo-3-phenylpropanoate and pyridine), then filtrated, and the resulted solids were washed with water, thereby pyridinium bromide was obtained.

The resulted pyridinium bromide, o-phthalaldehyde and p-methoxyacetophenone (2:1:2 in molar ratio) were added into a three-necked flask. And then tetrahydrofuran (20 times (weight) of the total amount of the resulted pyridinium bromide, o-phthalaldehyde and p-methoxyacetophenone) and catalysis amount ammonium acetate (10 molar % of the resulted pyridinium bromide) were added therein. The mixtures were refluxed for 23 hours, then crude product was obtained. Finally the multi-aryl substituted pyridine derivative was obtained via recrystallization with o-dichlorobenzene. The yield was about 60%9.

m/z: 740.29 (100.0%), 741.29 (53.3%), 742.30 (13.6%), 743.30 (2.9%), 742.29 (1.6%)

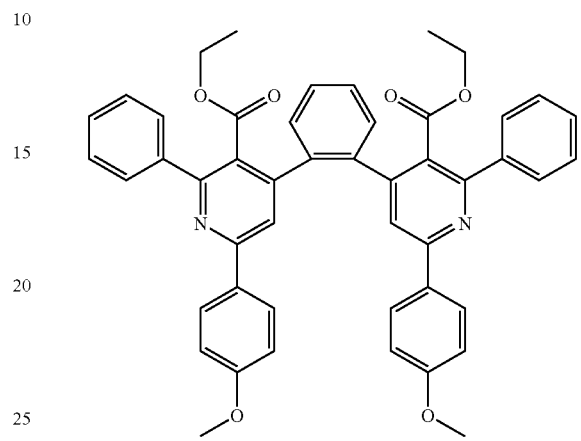

OLED device using compound PBNN II as ETL

Device structure as FIG. 2:

ITO/NPB(75 nm)/ADN(30 nm)/PBNN II (35 nm)/LiF(0.5 nm)/MgAg(100 nm)

CIE coordinate: X=0.14, Y=0.08

Turn-on voltage: 4.0V

Maximal brightness: 19850 cd/m$^2$ (12V)

Current efficiency: 4.8 cd/A

Example 46

Synthesis of 4,4'-(1,2-phenylene) bis(2-phenyl-6-p-tolylpyridine-3,5-dicarbonitrile) (PBPTDB)

2-bromo-3-oxo-3-phenylpropanenitrile and pyridine (1:1 in molar ratio) were stirred at 25° C. for 10 hours in ethanol (20 times (weight) of the total amount of 2-bromo-3-oxo-3-phenylpropanenitrile and pyridine), then filtrated, and the resulted solids were washed with water, thereby pyridinium bromide was obtained.

The resulted pyridinium bromide, 3-oxo-3-p-tolylpropanenitrile and o-phthalaldehyde (2:2:1 in molar ratio) were added into a three-necked flask. And then dipxane (20 times (weight) of the total amount of the resulted pyridinium bromide, 3-oxo-3-p-tolylpropanenitrile and o-phthalaldehyde) and catalysis amount ammonium acetate (10 molar % of the resulted pyridinium bromide) were added therein. The mixtures were refluxed for 29 hours, then crude product was obtained. Finally the multi-aryl substituted pyridine derivative was obtained via recrystallization with o-dichlorobenzene. The yield was about 45%.

m/z: 664.24 (100.0%), 665.24 (50.1%), 666.24 (13.2%), 665.23 (2.2%), 667.25 (2.0%)

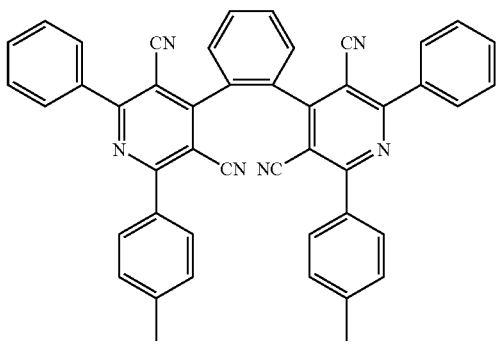

OLED device using compound PBPTDB as ETL
Device structure as FIG. 2:
ITO/NPB(70 nm)/5 tw % DSA-Ph:MADN(40)/PBPTDB (20 nm)/LiF(0.5)/Al(100 nm)
CIE coordinate: X=0.14, Y=0.21
Turn-on voltage: 4.1V
Maximal brightness: 20000 cd/m² (12V)
Current efficiency: 10 cd/A Example 47

Synthesis of 4,4'-(1,2-phenylene)bis(2-(4-tert-butylphenyl)-6-phenylpyridine-3,5-dicarbonitrile) (PBPPD II)

2-bromo-3-oxo-3-phenylpropanenitrile and pyridine (1:1 in molar ratio) were stirred at 25° C. for 11 hours in methanol (20 times (weight) of the total amount of 2-bromo-3-oxo-3-phenylpropanenitrile and pyridine), then filtrated, and the resulted solids were washed with water, thereby pyridinium bromide was obtained.
The resulted pyridinium bromide, 3-(4-tert-butylphenyl)-3-oxopropanenitrile and o-phthalaldehyde (3:3:1 in molar ratio) were added into a three-necked flask. And then acetic acid (20 times (weight) of the total amount of the resulted pyridinium bromide, 3-(4-tert-butylphenyl)-3-oxopropanenitrile and o-phthalaldehyde) and catalysis amount ammonium acetate (10 molar % of the resulted pyridinium bromide) were added therein. The mixtures were refluxed for 23 hours, then crude product was obtained. Finally the multi-aryl substituted pyridine derivative was obtained via silicon gel chromatography column with CH₂Cl₂/Petroleum ether (3:1 v/v) as the eluent. The yield was about 50%.
m/z: 748.33 (100.0%), 749.33 (58.5%), 750.34 (15.8%), 751.34 (3.2%), 750.33 (1.3%)

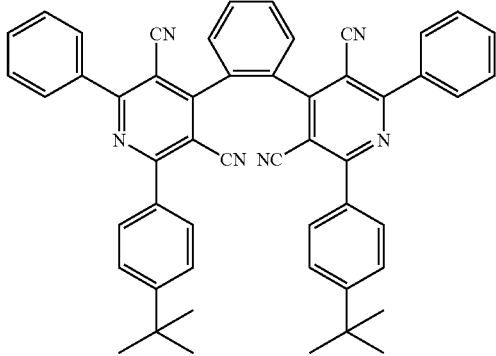

OLED device using compound PBPPD II as ETL
Device structure as FIG. 2:
ITO/NPB(75 nm)/ADN:TBP(30 nm)/PBPPD II (35 nm)/LiF(0.5 nm)/MgAg(100 nm)
CIE coordinate: X=0.15, Y=0.22
Turn-on voltage: 3.8V
Maximal brightness: 21200 cd/m² (12V)
Current efficiency: 5.0 cd/A Example 48

Synthesis of 1,2-bis(6-(furan-2-yl)-2-phenyl-3-(trifluoromethyl)pyridin-4-yl)benzene (BFTPB II)

2-bromo-3,3,3-trifluoro-1-phenylpropan-1-one and pyridine (1:1 in molar ratio) were stirred at 25° C. for 13 hours in dichloromethane (20 times (weight) of the total amount of 2-bromo-3,3,3-trifluoro-1-phenylpropan-1-one and pyridine), then filtrated, and the resulted solids were washed with water, thereby pyridinium bromide was obtained.
The resulted pyridinium bromide, o-phthalaldehyde and 1-(furan-2-yl)ethanone (2:1:2 in molar ratio) were added into a three-necked flask. And then tetrahydrofuran (20 times (weight) of the total amount of the resulted pyridinium bromide, o-phthalaldehyde and 1-(furan-2-yl)ethanone) and catalysis amount ammonium acetate (10 molar % of the resulted pyridinium bromide) were added therein. The mixtures were refluxed for 27 hours, then crude product was obtained. Finally the multi-aryl substituted pyridine derivative was obtained via silicon gel chromatography column with CH₂Cl₂/Petroleum ether(3:1 v/v) as the eluent. The yield was about 65%.
m/z: 652.16 (100.0%), 653.16 (42.2%), 654.17 (8.4%), 655.17 (1.3%)

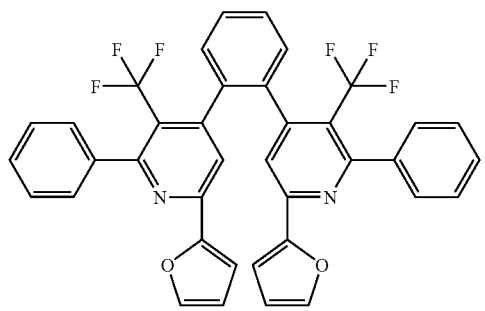

OLED device using compound BFTPB II as ETL
Device structure as FIG. 2:
ITO/NPB (30 nm)/6 wt % FIrpic:CBP (30 nm)/BFTPB II (30 nm)/LiF(0.5)/Al(100 nm)
CIE coordinate: X=0.15, Y=0.19
Turn-on voltage: 4.0V
Maximal brightness: 20000 cd/m² (12V)
Current efficiency: 12 cd/A.

What is claimed is:
1. An organic compound having electron-transporting and/or hole-blocking performance, wherein said organic compound is one of multi-aryl substituted pyridine derivatives represented by the following formulas (a)-(f):
wherein said organic compound is one of multi-aryl substituted pyridine derivatives represented by the following formulas (g)-(l):

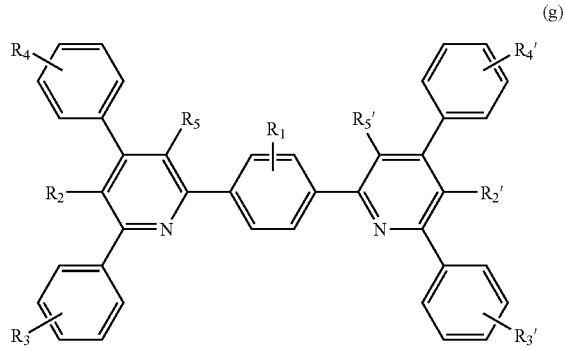
(g)

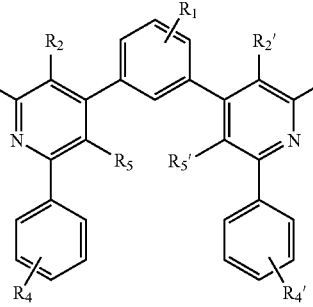
(k)

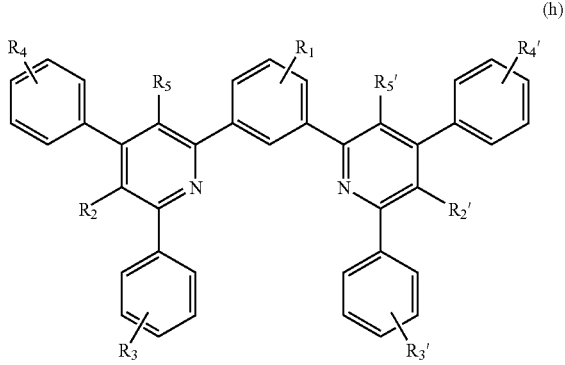
(h)

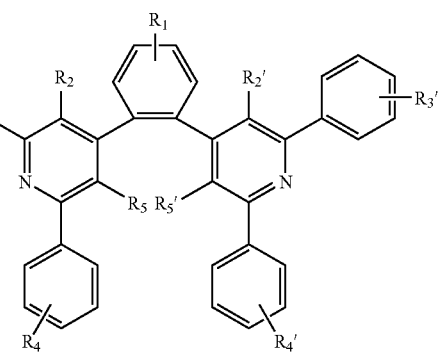
(l)

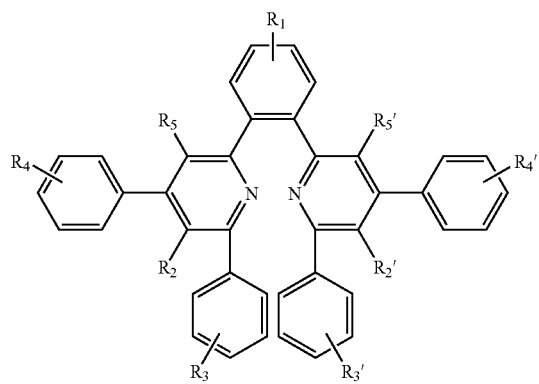
(i)

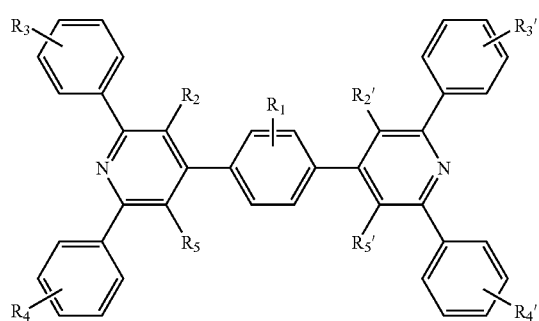
(j)

wherein $R_1$ in each formula is one independently selected from the group consisting of hydrogen, substituted or unsubstituted $C_1$-$C_{20}$ alkyl, substituted or unsubstituted $C_3$-$C_{20}$ cyclic alkyl, substituted or unsubstituted $C_1$-$C_{20}$ alkoxy, $C_7$-$C_{50}$ aralkyl, $C_6$-$C_{50}$ aryl and $C_6$-$C_{50}$ aryloxy:

$R_2$ $R_2'$, $R_5$, $R_5'$ in each formula are independently selected from the group consisting of hydrogen, carboxyl, fluorinated methyl, cyano, nitro and $C_2$-$C_{20}$ ester group, and at least one of $R_2$, $R_2'$, $R_5$, and $R_5'$ is selected from the group consisting of carboxyl, fluorinated methyl and cyano group;

$R_3$, $R_3'$, $R_4$, $R_4'$ in each formula are independently selected from the group consisting of hydrogen, substituted or unsubstituted $C_1$-$C_{20}$ alkyl, substituted or unsubstituted $C_3$-$C_{20}$ cyclic alkyl, substituted or unsubstituted $C_1$-$C_{20}$ substituent alkoxy, $C_7$-$C_{50}$ aralkyl, $C_6$-$C_{50}$ aryl and $C_6$-$C_{50}$ aryloxy.

2. The organic compound of claim 1, wherein said unsubstituted $C_1$-$C_{20}$ alkyl is methyl, ethyl, propyl, isopropyl, n-butyl, sec-butyl, isobutyl, tert-butyl, n-pentyl, n-hexyl, n-heptyl or n-octyl;

said substituted $C_1$-$C_{20}$ alkyl is hydroxymethyl, 1-hydroxyethyl, 2-hydroxyethyl, 2-hydroxy-isobutyl, 1,2-dihydroxy-ethyl, 1,3-dihydroxy-isopropyl, 2,3-dihydroxy-tert-butyl, 1,2,3-trihydroxy-propyl, chloromethyl, 1-chloroethyl, 2-chloroethyl, 2-chloroisobutyl, 1,2-dichloroethyl, 1,3-dichloro-isopropyl, 2,3-dichloro-tert-butyl, 1,2,3-trichloropropyl, bromomethyl, 1-bromoethyl, 2-bromoethyl, 2-bromo-isobutyl, 1,2-dibromoethyl, 2-bromo-isobutyl, 1,2-dibromoethyl, 1,3-dibromo- isopropyl, 2,3-dibromo-tert-butyl, 1,2,3-tribromopropyl, iodomethyl, 1-iodoethyl, 2-iodoethyl, 2-iodo- isobutyl, 1,2-diiodoethyl, 1,3-diiodo-isopropyl, 2,3-diiodo-tert-butyl, 1,2,3-triiodopropyl, aminomethyl, 1-aminoethyl,2-amino-tert-ethyl, 2-amino-isobutyl, 1,2-diaminoethyl, 1,3-diaminoisopropyl, 2,3-diamino-tert-butyl or 1,2,3-triaminopropyl;

said unsubstituted $C_3$-$C_{20}$ cyclic alkyl is cyclopropyl, cyclobutyl, cyclopentyl or cyclohexyl;

said substituted $C_3$-$C_{20}$ cyclic alkyl is 4-methyl-cyclohexyl, adamantyl or norbornyl;

said $C_1$-$C_{20}$ alkoxy is represented by —OR, wherein R is methyl, ethyl, propyl, isopropyl, n-butyl, sec-butyl, isobutyl, tert-butyl, n-pentyl, n-hexyl, n-heptyl, n-octyl, hydroxymethyl, 1-hydroxyethyl, 2-hydroxyethyl, 2-hydroxy-isobutyl, 1,2-dihydroxy-ethyl, 1,3-dihydroxy-isopropyl, 2,3-dihydroxy-tert-butyl, 1,2,3-trihydroxy-propyl, chloromethyl, 1-chloroethyl, 2-chloroethyl, 2-chloroisobutyl, 1,2-dichloroethyl, 1,3-dichloro-isopropyl, 2,3-dichloro-tert-butyl, 1,2,3-trichloropropyl, bromomethyl, 1-bromoethyl, 2-bromoethyl, 2-bromo-isobutyl, 1,2-dibromoethyl, 2-bromo-isobutyl, 1,2-dibromoethyl, 1,3-dibromo-isopropyl, 2,3-dibromo-tert-butyl, 1,2,3-tribromopropyl, iodomethyl, 1-iodoethyl, 2-iodoethyl, 2-iodo-isobutyl, 1,2-diiodoethyl, 1,3-diiodo-isopropyl, 2,3-diiodo-tert-butyl, 1,2,3-triiodopropyl, aminomethyl, 1-aminoethyl, 2-aminoethyl, 2-amino-isotutyl, 1,2-diaminoethyl, 1,3-diaminoisopropyl, 2,3-diamino-tert-butyl, 1,2,3-triaminopropyl, cyanometyhyl, 1-cyanoethyl, 2-cyanoethyl, 2-cyanoisobutyl, 1,2-dicyanoethyl, 1,3-dicyano-isopropyl, 2,3-dicyano-tert-butyl, 1,2,3-tricyanopropyl, nitromethyl, 1-nitroethyl, 2-nitroethyl, 2-nitro-isobutyl, 1,2-dinitroethyl, 1,3-dinitro-isopropyl, 2,3-dinitro-tert-butyl or 1,2,3-trinitropropyl;

said $C_7$-$C_{50}$ aralkyl is benzyl, 1-phenylethyl, 2-phenylethyl, 1-phenyl-isopropyl, 2-phenyl-isopropyl, phenyl-tert-butyl, α-naphthyl-methyl, 1-α-naphthylethyl, 2-α-naphthylethyl, 1-α-naphthyl-isopropyl, 2-α-naphthyl-isopropyl, β-naphthylmethyl, 1-β-naphthylethyl, 2-β-naphthylethyl, 1-β-naphthyl-isopropyl, 2-β-naphthyl-isopropyl, 1-pyrrylmethyl, 2-(1-pyrryl)ethyl, p-methylbenzyl, m-methylbenzyl, o-methylbenzyl p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-chloro-2-phenyl-isopropyl or triphenylmethyl;

said $C_6$-$C_{50}$ aryl is phenyl, 1-naphthyl, 2-naphthyl, 1-anthracenyl, 2-anthracenyl, 9-anthracenyl, 1-phenanthryl, 2-phenanthryl, 3-phenanthryl, 4-phenanthryl, 9-phenanthryl, 1-tetraphenyl, 2-tetraphenyl, 9-tetraphenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthracene, 4'-methyl-biphenyl or 4"-tert-butyl-p-terphenyl-4-yl;

said $C_6$-$C_{50}$ aryloxyl is represented by —OAr wherein Ar is phenyl, 1-naphthyl, 2-naphthyl, 1-anthracenyl, 2-anthracenyl, 9-anthracenyl, 1-phenanthryl, 2-phenanthryl, 3-phenanthryl, 4-phenanthryl, 9-phenanthryl, 1-tetraphenyl, 2-tetraphenyl, 9-tetraphenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthracene, 4'-methyl-1-naphthyl, 4-methyl-1-anthracene, 4'-methyl-biphenyl, 4"-tert-butyl-p-terphenyl-4-yl, 2-pyrrolyl, 3-pyrrolyl, 1-pyridyl, 2-pyridyl, 3-pyridyl, 4-pyridyl, 2-indolyl, 3-indolyl, 4-indolyl, 5-indolyl, 6-indolyl, 7-indolyl, 8-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 5-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenathiazinyl, 2-phenathiazinyl, 3-phenathiazinyl, 4-phenathiazinyl, 1-phenoxazinyl, 2-phenoxazinyl, 3-phenoxazinyl, 4-phenoxazinyl, 2-oxazol, 4-oxazol, 5-oxazol, 2-oxadiazol, 5-oxadiazol, 3-furazano, 2-trienyl, 3-trienyl, 2-methylpyridine-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-tert-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl;

said fluorinated methyl is fluoromethyl, difluoromethyl, or trifluoromethyl;

said $C_2$-$C_{20}$ ester group is methyl ester group, ethyl ester group, propyl ester group, isopropyl ester group, n-butyl ester group, sec-butyl ester group, isobutyl ester group, n-hexyl ester group, n-heptyl ester group or n-octyl ester group.

3. An OLED comprising an anode, a cathode, an emitting layer disposed between said anode and said cathode, at least one hole-transporting layer disposed between said anode and said emitting layer, at least one electron-transporting layer disposed between said cathode and said emitting layer, and a substrate present on either the anode or cathode, wherein said at least one of electron-transporting layer comprises an organic compound which is one of multi-aryl substituted pyridine derivatives represented by the following formulas (a)-(f):

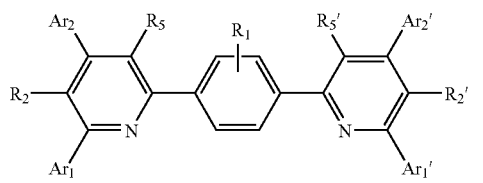
(a)

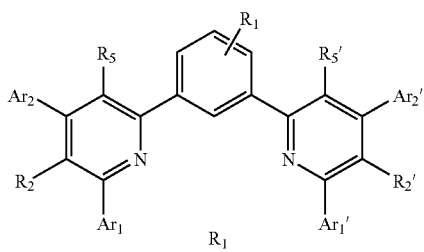
(b)

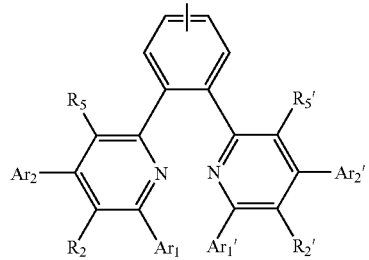
(c)

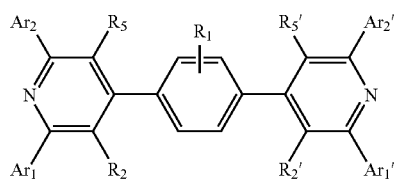
(d)

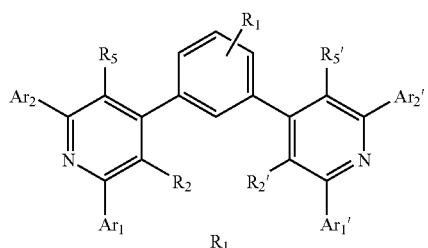
(e)

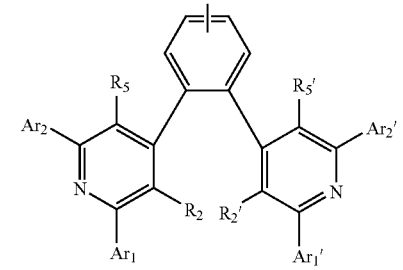
(f)

wherein:

$R_1$ in each formula is one independently selected from the group consisting of hydrogen, substituted or unsubstituted $C_1$-$C_{20}$ alkyl, substituted or unsubstituted $C_3$-$C_{20}$ cyclic alkyl, substituted or unsubstituted $C_1$-$C_{20}$ alkoxy, $C_7$-$C_{50}$ aralkyl, $C_6$-$C_{50}$ aryl, $C_6$-$C_{50}$ aryloxy and $C_5$-$C_{50}$ heterocyclic aryl;

$R_2$, $R_2'$, $R_5$, $R_5'$ in each formula are independently selected from the group consisting of hydrogen, carboxyl, fluorinated methyl, cyano, nitro and $C_2$-$C_{20}$ ester group, and at least one of $R_2$, $R_2'$, $R_5$, and $R_5'$ is selected from the group consisting of carboxyl, fluorinated methyl and cyano group;

$Ar_1$, $Ar_1'$, $Ar_2$, $Ar_2'$ in each formula are independently selected from the group consisting of $C_6$-$C_{50}$ aryl and $C_5$-$C_{50}$ heterocyclic aryl.

4. An OLED comprising an anode, a cathode, an emitting layer disposed between said anode and said cathode, at least one hole-transporting layer disposed between said anode and said emitting layer, at least one electron-transporting layer disposed between said cathode and said emitting layer, at least one hole-blocking layer between the emitting layer and the electron-transporting layer, and a substrate present on either the anode or cathode, wherein said at least one of hole-blocking layer comprises an organic compound which is one of multi-aryl substituted pyridine derivatives represented by the following formulas (a)-(f):

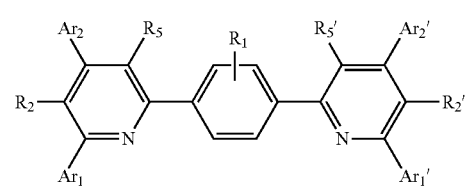
(a)

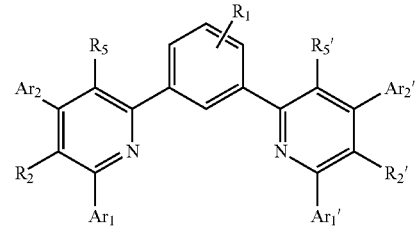
(b)

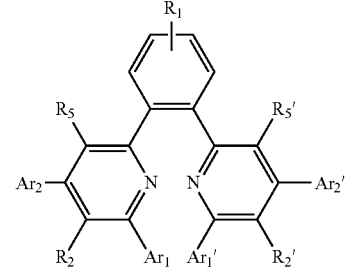
(c)

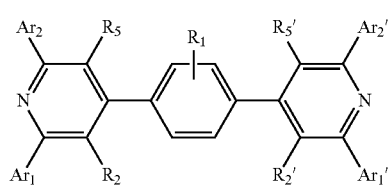
(d)

(e)

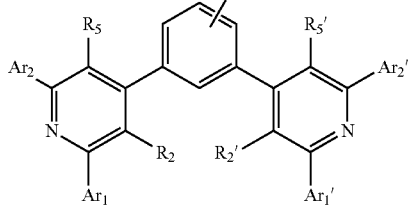

(f)

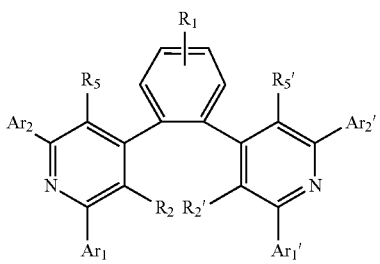

wherein:
R₁ in each formula is one independently selected from the group consisting of hydrogen, substituted or unsubstituted $C_1$-$C_{20}$ alkyl, substituted or unsubstituted $C_3$-$C_{20}$ cyclic alkyl, substituted or unsubstituted $C_1$-$C_{20}$ alkoxy, $C_7$-$C_{50}$ aralkyl, $C_6$-$C_{50}$ aryl, $C_6$-$C_{50}$ aryloxy and $C_5$-$C_{50}$ heterocyclic aryl;

$R_2$, $R_2'$, $R_5$, $R_5'$ in each formula are independently selected from the group consisting of hydrogen, carboxyl, fluorinated methyl, cyano, nitro and $C_2$-$C_{20}$ ester group, and at least one of $R_2$, $R_2'$, $R_5$, and $R_5'$ is selected from the group consisting of carboxyl, fluorinated methyl and cyano group;

$Ar_1$, $Ar_1'$, $Ar_2$, $Ar_2'$ in each formula are independently selected from the group consisting of $C_6$-$C_{50}$ aryl and $C_5$-$C_{50}$ heterocyclic aryl.

5. An OLED comprising an anode, a cathode, an emitting layer disposed between said anode and said cathode, at least one hole-transporting layer disposed between said anode and said emitting layer, at least one electron-transporting layer disposed between said cathode and said emitting layer, and a substrate present on either the anode or cathode, wherein said at least one of electron-transporting layer comprises an organic compound which is one of multi-aryl substituted pyridine derivatives represented by the following formulas (g)-(l):

(g)

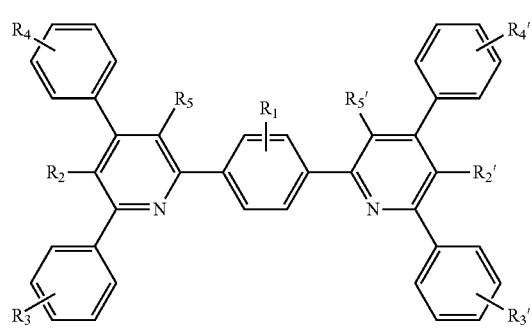

(h)

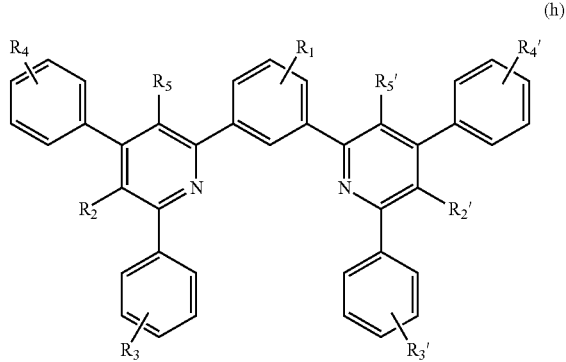

(i)

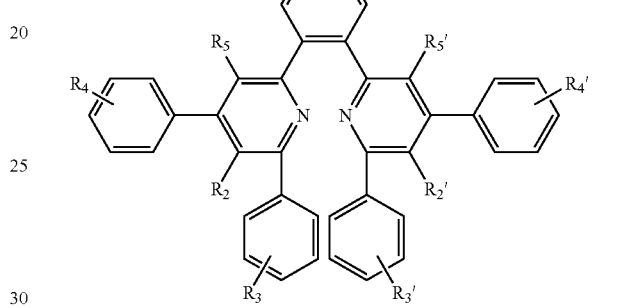

(j)

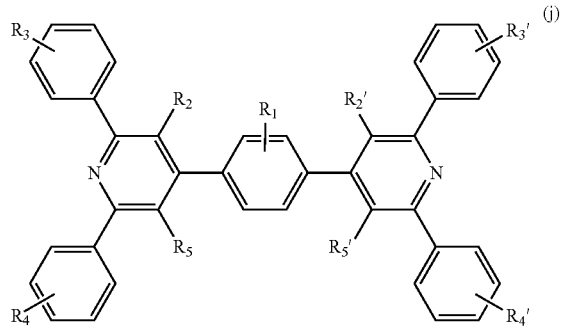

wherein
R₁ in each formula is one independently selected from the group consisting of hydrogen, substituted or unsubstituted $C_1$-$C_{20}$ alkyl substituted or unsubstituted $C_3$-$C_{20}$ cyclic alkyl, substituted or unsubstituted $C_1$-$C_{20}$ alkoxy, $C_7$-$C_{50}$ aralkyl, $C_6$-$C_{50}$ aryl, $C_6$-$C_{50}$ aryloxy and $C_5$-$C_{50}$ heterocyclic aryl;

$R_2$ $R_2'$, $R_5$, $R_5'$ in each formula are independently selected from the group consisting of hydrogen, carboxyl, fluorinated methyl, cyano, nitro and $C_2$-$C_{20}$ ester group, carboxyl, fluorinated methyl and cyano group;

$R_3$, $R_3'$, $R_4$, $R_4'$ in each formula is independently selected from the group consisting of hydrogen, substituted or unsubstituted $C_1$-$C_{20}$ alkyl, substituted or unsubstituted $C_3$-$C_{20}$ cyclic alkyl, substituted or unsubstituted $C_1$-$C_{20}$ substituent alkoxy, $C_7$-$C_{50}$ aralkyl, $C_6$-$C_{50}$ aryl, $C_6$-$C_{50}$ aryloxy and $C_5$-$C_{50}$ heterocyclic aryl.

6. The OLED of claim 5, wherein said unsubstituted $C_1$-$C_{20}$ alkyl is methyl, ethyl, propyl, isopropyl, n-butyl, sec-butyl, isobutyl, tert-butyl, n-pentyl, n-hexyl, n-heptyl or n-octyl;

said substituted $C_1$-$C_{20}$ alkyl is hydroxymethyl, 1-hydroxyethyl, 2-hydroxyethyl, 2-hydroxy-isobutyl, 1,2-dihydroxy-ethyl, 1,3-dihydroxy-isopropyl, 2,3-dihydroxy-tert-butyl, 1,2,3-trihydroxy-propyl, chloromethyl, 1-chloroethyl, 2-chloroethyl, 2-chloroisobutyl, 1,2-dichloroethyl, 1,3-dichloro-isopropyl, 2,3-dichloro-tert-butyl, 1,2,3-trichloropropyl, bromomethyl, 1-bromoethyl, 2-bromoethyl, 2-bromo-isobutyl, 1,2-dibromoethyl, 2-bromo-isobutyl, 1,2-dibromoethyl, 1,3-dibromo- isopropyl, 2,3-dibromo-tert-butyl, 1,2,3-tribromopropyl, iodomethyl, 1-iodoethyl, 2-iodoethyl, 2-iodo- isobutyl, 1,2-diiodoethyl, 1,3-diiodo-isopropyl, 2,3-diiodo-tert-butyl, 1,2,3-triiodopropyl, aminomethyl, 1-aminoethyl, 2-amino-tert-ethyl, 2-amino-isotutyl, 1,2-diaminoethyl, 1,3-diaminoisopropyl, 2,3-diamino-tert-butyl or 1,2,3-triaminopropyl;

said unsubstituted $C_3$-$C_{20}$ cyclic alkyl is cyclopropyl, cyclobutyl, cyclopentyl or cyclohexyl;

said substituted $C_3$-$C_{20}$ cyclic alkyl is 4-methyl-cyclohexyl, adamantyl or norbornyl;

said $C_1$-$C_{20}$ alkoxy is represented by —OR, wherein R is methyl, ethyl, propyl, isopropyl, n-butyl, sec-butyl, isobutyl, tert-butyl, n-pentyl, n-hexyl, n-heptyl, n-octyl, hydroxymethyl, 1-hydroxyethyl, 2-hydroxyethyl, 2-hydroxy-isobutyl, 1,2-dihydroxy-ethyl, 1,3-dihydroxy-isopropyl, 2,3-dihydroxy-tert-butyl, 1,2,3-trihydroxy-propyl, chloromethyl, 1-chloroethyl, 2-chloroethyl, 2-chloroisobutyl, 1,2-dichloroethyl, 1,3-dichloro-isopropyl, 2,3-dichloro-tert-butyl, 1,2,3-trichloropropyl, bromomethyl, 1-bromoethyl, 2-bromoethyl, 2-bromo-isobutyl, 1,2-dibromoethyl, 2-bromo-isobutyl, 1,2-dibromoethyl, 1,3-dibromo- isopropyl, 2,3-dibromo-tert-butyl, 1,2,3-tribromopropyl, iodomethyl, 1-iodoethyl, 2-iodoethyl, 2-iodo-isobutyl, 1,2-diiodoethyl, 1,3-diiodo-isopropyl, 2,3-diiodo-tert-butyl, 1,2,3-triiodopropyl, aminomethyl, 1-aminoethyl, 2-aminoethyl, 2-amino-isotutyl, 1,2-diaminoethyl, 1,3-diaminoisopropyl, 2,3-diamino-tert-butyl, 1,2,3-triaminopropyl, cyanometyhyl, 1-cyanoethyl, 2-cyanoethyl, 2-cyano-isobutyl, 1,2-dicyanoethyl, 1,3-dicyano-isopropyl, 2,3-dicyano-tert-butyl, 1,2,3-tricyanopropyl, nitromethyl, 1-nitroethyl, 2-nitroethyl, 2-nitro-isobutyl, 1,2-dinitroethyl, 1,3-dinitro-isopropyl, 2,3-dinitro-tert-butyl or 1,2,3-trinitropropyl;

said $C_7$-$C_{50}$ aralkyl is benzyl, 1-phenylethyl, 2-phenylethyl, 1-phenyl-isopropyl, 2-phenyl-isopropyl, phenyl-tert-butyl, α-naphthyl-methyl, 1-α-naphthylethyl, 2-α-naphthylethyl, 1-α-naphthyl-isopropyl, 2-α-naphthyl-isopropyl, β-naphthylmethyl, 1-β-naphthylethyl, 2-β-naphthylethyl, 1-β-naphthyl-isopropyl, 2-β-naphthyl-isopropyl, 1-pyrrylmethyl, 2-(1-pyrryl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-chloro-2-phenyl-isopropyl or triphenylmethyl;

said $C_6$-$C_{50}$ aryl is phenyl, 1-naphthyl, 2-naphthyl, 1-anthracenyl, 2-anthracenyl, 9-anthracenyl, 1-phenanthryl, 2-phenanthryl, 3-phenanthryl, 4-phenanthryl, 9-phenanthryl, 1-tetraphenyl, 2-tetraphenyl, 9-tetraphenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthracene, 4'-methyl-biphenyl or 4"-tert-butyl-p-terphenyl-4-yl;

said $C_6$-$C_{50}$ aryloxyl is represented by —OAr wherein Ar is phenyl, 1-naphthyl, 2-naphthyl, 1-anthracenyl, 2-anthracenyl, 9-anthracenyl, 1-phenanthryl, 2-phenanthryl, 3-phenanthryl, 4-phenanthryl, 9-phenanthryl, 1-tetraphenyl, 2-tetraphenyl, 9-tetraphenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthracene, 4'-methyl-biphenyl, 4"-tert-butyl-p-terphenyl-4-yl, 2-pyrrolyl, 3-pyrrolyl, 1-pyridyl, 2-pyridyl, 3-pyridyl, 4-pyridyl, 2-indolyl, 3-indolyl, 4-indolyl, 5-indolyl, 6-indolyl, 7-indolyl, 8-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 5-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenathiazinyl, 2-phenathiazinyl, 3-phenathiazinyl, 4-phenathiazinyl, 1-phenoxazinyl, 2-phenoxazinyl, 3-phenoxazinyl, 4-phenoxazinyl, 2-oxazol, 4-oxazol, 5-oxazol, 2-oxadiazol, 5-oxadiazol, 3-furazano, 2-trienyl, 3-trienyl, 2-methylpyridine-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-tert-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl;

said $C_5$-$C_{50}$ heterocyclic aryl is 2-pyrrolyl, 3-pyrrolyl, 1-pyridyl, 2-pyridyl, 3-pyridyl, 4-pyridyl, 2-indolyl, 3-indolyl, 4-indolyl, 5-indolyl, 6-indolyl, 7-indolyl, 8-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 5-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenathiazinyl, 2-phenathiazinyl, 3-phenathiazinyl, 4-phenathiazinyl, 1-phenoxazinyl, 2-phenoxazinyl, 3-phenoxazinyl, 4-phenoxazinyl, 2-oxazol, 4-oxazol, 5-oxazol, 2-oxadiazol, 5-oxadiazol, 3-furazano, 2-trienyl, 3-trienyl, 2-methylpyridine-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-tert-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl;

said fluorinated methyl is fluoromethyl, difluoromethyl, or trifluoromethyl;

said $C_2$-$C_{20}$ ester group is methyl ester group, ethyl ester group, propyl ester group, isopropyl ester group, n-butyl ester group, sec-butyl ester group, isobutyl ester group, n-hexyl ester group, n-heptyl ester group or n-octyl ester group.

7. An OLED comprising an anode, a cathode, an emitting layer disposed between said anode and said cathode, at least one hole-transporting layer disposed between said anode and said emitting layer, at least one electron-transporting layer disposed between said cathode and said emitting layer, at least one hole-blocking layer between the emitting layer and the electron-transporting layer, and a substrate present on either the anode or cathode, wherein said at least one of hole-blocking layer comprises an organic compound which is one of multi-aryl substituted pyridine derivatives represented by the following formulas (g)-(l):

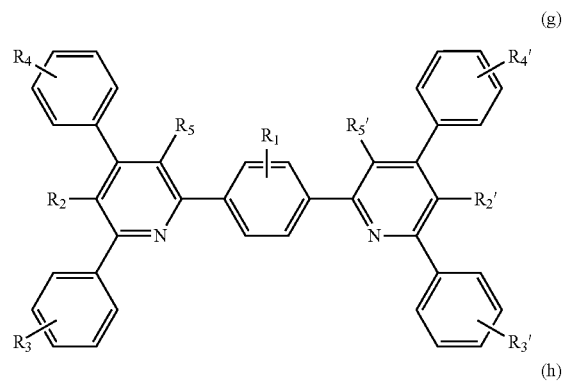

(g)

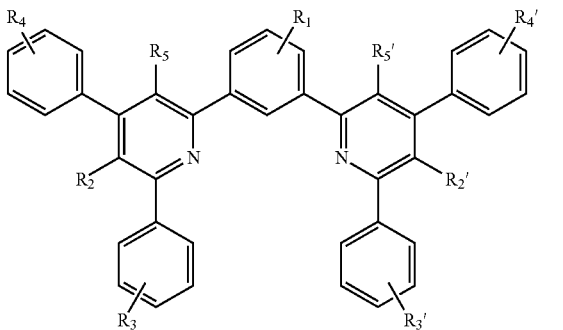

(h)

wherein $R_1$ in each formula is one independently selected from the group consisting of hydrogen, substituted or unsubstituted $C_1$-$C_{20}$ alkyl, substituted or unsubstituted $C_3$-$C_{20}$ cyclic alkyl, substituted or unsubstituted $C_1$-$C_{20}$ alkoxy, $C_7$-$C_{50}$ aralkyl, $C_6$-$C_{50}$ aryl, $C_6$-$C_{50}$ aryloxy and $C_5$-$C_{50}$ heterocyclic aryl;

$R_2$, $R_2'$, $R_5$, $R_5'$ in each formula are independently selected from the group consisting of hydrogen, carboxyl, fluorinated methyl, cyano, nitro and $C_2$-$C_{20}$ ester group, carboxyl, fluorinated methyl and cyano group;

$R_3$, $R_3'$, $R_4$, $R_4'$ in each formula is independently selected from the group consisting of hydrogen, substituted or unsubstituted $C_1$-$C_{20}$ alkyl, substituted or unsubstituted $C_3$-$C_{20}$ cyclic alkyl, substituted or unsubstituted $C_1$-$C_{20}$ substituent alkoxy, $C_7$-$C_{50}$ aralkyl, $C_6$-$C_{50}$ aryl, $C_6$-$C_{50}$ aryloxy and $C_5$-$C_{50}$ heterocyclic aryl.

8. The OLED of claim 7, wherein said unsubstituted $C_1$-$C_{20}$ alkyl is methyl, ethyl, propyl, isopropyl, n-butyl, sec-butyl, isobutyl, tert-butyl, n-pentyl, n-hexyl, n-heptyl or n-octyl;

said substituted $C_1$-$C_{20}$ alkyl is hydroxymethyl, 1-hydroxyethyl, 2-hydroxyethyl, 2-hydroxy-isobutyl, 1,2-dihydroxy-ethyl, 1,3-dihydroxy-isopropyl, 2,3-dihydroxy-tert-butyl, 1,2,3-trihydroxy-propyl, chloromethyl, 1-chloroethyl, 2-chloroethyl, 2-chloroisobutyl, 1,2-dichloroethyl, 1,3-dichloro-isopropyl, 2,3-dichloro-tert-butyl, 1,2,3-trichloropropyl, bromomethyl, 1-bromoethyl, 2-bromoethyl, 2-bromo-isobutyl, 1,2-dibromoethyl, 2-bromo-isobutyl, 1,2-dibromoethyl, 1,3-dibromo- isopropyl, 2,3-dibromo-tert-butyl, 1,2,3-tribromopropyl, iodomethyl, 1-iodoethyl, 2-iodoethyl, 2-iodo-isobutyl, 1,2-diiodoethyl, 1,3-diiodo-isopropyl, 2,3-diiodo-tert-butyl, 1,2,3-triiodopropyl, aminomethyl, 1-aminoethyl, 2-amino-tert-ethyl, 2-amino-isotutyl, 1,2-diaminoethyl, 1,3-diaminoisopropyl, 2,3-diamino-tert-butyl or 1,2,3-triaminopropyl;

said unsubstituted $C_3$-$C_{20}$ cyclic alkyl is cyclopropyl, cyclobutyl, cyclopentyl or cyclohexyl;

said substituted $C_3$-$C_{20}$ cyclic alkyl is 4-methyl-cyclohexyl, adamantyl or norbornyl;

said $C_1$-$C_{20}$ alkoxy is represented by —OR, wherein R is methyl, ethyl, propyl, isopropyl, n-butyl, sec-butyl, isobutyl, tert-butyl, n-pentyl, n-hexyl, n-heptyl, n-octyl, hydroxymethyl, 1-hydroxyethyl, 2-hydroxyethyl, 2-hydroxy-isobutyl, 1,2- dihydroxy-ethyl, 1,3-dihydroxy-isopropyl, 2,3-dihydroxy-tert-butyl, 1,2,3-trihydroxy-propyl, chloromethyl, 1-chloroethyl, 2-chloroethyl, 2-chloroisobutyl, 1,2-dichloroethyl, 1,3-dichloro-isopropyl, 2,3-dichloro-tert-butyl, 1,2,3-trichloropropyl, bromomethyl, 1-bromoethyl, 2-bromoethyl, 2-bromo-isobutyl, 1,2-dibromoethyl, 2-bromo-isobutyl, 1,2-dibromoethyl, 1,3-dibromo-isopropyl, 2,3-dibromo-tert-butyl, 1,2,3-tribromopropyl, iodomethyl, 1-iodoethyl, 2-iodoethyl, 2-iodo-isobutyl, 1,2-diiodoethyl, 1,3-diiodo-isopropyl, 2,3-diiodo-tert-butyl, 1,2,3-triiodopropyl, aminomethyl, 1-aminoethyl, 2-aminoethyl, 2-amino-isotutyl, 1,2-diaminoethyl, 1,3-diaminoisopropyl, 2,3-diamino-tert-butyl, 1,2,3-triaminopropyl, cyanometyhyl, 1-cyanoethyl, 2-cyanoethyl, 2-cyanoisobutyl, 1,2-dicyanoethyl, 1,3-dicyano-isopropyl, 2,3-dicyano-tert-butyl, 1,2,3-tricyanopropyl, nitromethyl, 1-nitroethyl, 2-nitroethyl, 2-nitro-isobutyl, 1,2-dinitroethyl, 1,3-dinitro-isopropyl, 2,3-dinitro-tert-butyl or 1,2,3-trinitropropyl;

said $C_7$-$C_{50}$ aralkyl is benzyl, 1-phenylethyl, 2-phenylethyl, 1-phenyl-isopropyl, 2-phenyl-isopropyl, phenyl-tert-butyl, α-naphthyl-methyl, 1-α-naphthylethyl, 2-α-naphthylethyl, 1-α-naphthyl-isopropyl, 2-α-naphthyl-isopropyl, β-naphthylmethyl, 1-β-naphthylethyl, 2-β-naphthylethyl, 1-β-naphthyl-isopropyl, 2β-naphthyl-isopropyl, 1-pyrrylmethyl, 2-(1-pyrryl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-chloro-2-phenyl-isopropyl or triphenylmethyl;

said $C_6$-$C_{50}$ aryl is phenyl, 1-naphthyl, 2-naphthyl, 1-anthracenyl, 2-anthracenyl, 9-anthracenyl, 1-phenanthryl, 2-phenantryl, 3-phenanthryl, 4-phenanthryl, 9-phenanthryl, 1-tetraphenyl, 2-tetraphenyl, 9-tetraphenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthracene, 4'-methyl-biphenyl or 4"-tert-butyl-p-terphenyl-4-yl;

said $C_6$-$C_{50}$ aryloxyl is represented by —OAr wherein Ar is phenyl, 1-naphthyl, 2-naphthyl, 1-anthracenyl, 2-anthracenyl, 9-anthracenyl, 1-phenanthryl, 2-phenanthryl, 3-phenanthryl, 4-phenanthryl, 9-phenanthryl, 1-tetraphenyl, 2-tetraphenyl, 9-tetraphenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthracene, 4'-methyl-biphenyl, 4"-tert-butyl-p-terphenyl-4-yl, 2-pyrrolyl, 3-pyrrolyl, 1-pyridyl, 2-pyridyl, 3-pyridyl, 4-pyridyl, 2-indolyl, 3-indolyl, 4-indolyl, 5-indolyl, 6-indolyl, 7-indolyl, 8-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 5-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenathiazinyl, 2-phenathiazinyl, 3-phenathiazinyl, 4-phenathiazinyl, 1-phenoxazinyl, 2-phenoxazinyl, 3-phenoxazinyl, 4-phenoxazinyl, 2-oxazol, 4-oxazol, 5-oxazol, 2-oxadiazol, 5-oxadiazol, 3-furazano, 2-trienyl, 3-trienyl, 2-methylpyridine-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-tert-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl;

said $C_5$-$C_{50}$ heterocyclic aryl is 2-pyrrolyl, 3-pyrrolyl, 1-pyridyl, 2-pyridyl, 3-pyridyl, 4-pyridyl, 2-indolyl, 3-indolyl, 4-indolyl, 5-indolyl, 6-indolyl, 7-indolyl, 8-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 5-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenathiazinyl, 2-phenathiazinyl, 3-phenathiazinyl, 4-phenathiazinyl, 1-phenoxazinyl, 2-phenoxazinyl, 3-phenoxazinyl, 4-phenoxazinyl, 2-oxazol, 4-oxazol, 5-oxazol, 2-oxadiazol, 5-oxadiazol, 3-furazano, 2-trienyl, 3-trienyl, 2-methylpyridine-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-tert-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl;

said fluorinated methyl is fluoromethyl, difluoromethyl, or trifluoromethyl;

said $C_2$-$C_{20}$ ester group is methyl ester group, ethyl ester group, propyl ester group, isopropyl ester group, n-butyl ester group, sec-butyl ester group, isobutyl ester group, n-hexyl ester group, n-heptyl ester group or n-octyl ester group.

* * * * *